US010899702B2

(12) United States Patent
Xie et al.

(10) Patent No.: US 10,899,702 B2
(45) Date of Patent: Jan. 26, 2021

(54) HTRPVI CHEMICAL AGENTS

(71) Applicant: UNIVERSITY OF PITTSBURGH—OF THE COMMONWEALTH SYSTEM OF HIGHER EDUCATION, Pittsburgh, PA (US)

(72) Inventors: Xiang-Qun Xie, Sewickley, PA (US); Zhiwei Feng, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 0 days.

(21) Appl. No.: 15/546,833

(22) PCT Filed: Feb. 5, 2016

(86) PCT No.: PCT/US2016/016826
§ 371 (c)(1),
(2) Date: Jul. 27, 2017

(87) PCT Pub. No.: WO2016/127085
PCT Pub. Date: Aug. 11, 2016

(65) Prior Publication Data
US 2018/0215705 A1 Aug. 2, 2018

Related U.S. Application Data

(60) Provisional application No. 62/113,429, filed on Feb. 7, 2015.

(51) Int. Cl.
| | |
|---|---|
| *C07C 275/30* | (2006.01) |
| *C07C 275/34* | (2006.01) |
| *C07C 275/40* | (2006.01) |
| *C07C 275/42* | (2006.01) |
| *C07D 295/135* | (2006.01) |
| *C07C 275/32* | (2006.01) |

(52) U.S. Cl.
CPC .......... *C07C 275/30* (2013.01); *C07C 275/32* (2013.01); *C07C 275/34* (2013.01); *C07C 275/40* (2013.01); *C07C 275/42* (2013.01); *C07D 295/135* (2013.01)

(58) Field of Classification Search
CPC .................................................. C07C 275/30
See application file for complete search history.

(56) References Cited

U.S. PATENT DOCUMENTS

| | | | | |
|---|---|---|---|---|
| 6,262,113 B1 * | 7/2001 | Widdowson | ........... | A61K 31/17 514/522 |
| 7,517,880 B2 * | 4/2009 | Miller | .................... | A61K 31/17 514/237.8 |
| 7,521,480 B2 * | 4/2009 | Valgeirsson | .......... | C07C 275/42 514/646 |
| 2010/0261911 A1 | 10/2010 | Kenji et al. | | |

FOREIGN PATENT DOCUMENTS

| | | |
|---|---|---|
| WO | WO 03/093250 A2 | 11/2003 |
| WO | WO 2005/021721 A2 | 3/2005 |
| WO | WO 2010/146236 A1 | 12/2010 |

OTHER PUBLICATIONS

Valgeirsson et al (2004): STN International, HCAPLUS database (Columbus, Ohio), Accession No. 2004: 453168.*
Zhang et al (2010): STN International, HCAPLUS database (Columbus, Ohio), Accession No. 2010: 1132914.*
Sellergren et al (2012): STN International, HCAPLUS database (Columbus, Ohio), Accession No. 2016: 2074115.*
Kasahara et al (2010): STN International, HCAPLUS database (Columbus, Ohio), Accession No. 2016: 2068552.*
Goldfarb et al (2009): STN International, HCAPLUS database (Columbus, Ohio), Accession No. 2009: 846105.*
Giovannini et al (2012): STN International, HCAPLUS database (Columbus, Ohio), Accession No. 2012: 887319.*
Qiu et al (2011): STN International, HCAPLUS database (Columbus, Ohio), Accession No. 2016: 2081676.*
Widdowson et al (2001): STN International, HCAPLUS database (Columbus, Ohio), Accession No. 2001: 521916.*
Benson et al (2000): STN International, HCAPLUS database (Columbus, Ohio), Accession No. 2000: 900438.*
Beaver et al (1957): STN International, HCAPLUS database (Columbus, Ohio), Accession No. 1957: 62160.*
Cance et al (2008): STN International, HCAPLUS database (Columbus, Ohio), Accession No. 2008: 1157604.*
Anderson et al (2006): STN International, HCAPLUS database (Columbus, Ohio), Accession No. 2006: 826284.*
International Preliminary Report on Patentability issued in related International Patent Application No. PCT/US2016/016826, dated Aug. 17, 2017.
International Search Report and Written Opinion issued in related International Patent Application No. PCT/US2016/016826, dated May 10, 2016.
Trevisani et al., "TRPV1 antagonists as analogesic agents," *The Open Pain Journal*, vol. 6, pp. 108-118 (2013).
Notari, R.E., "Theory and Practice of Prodrug Kinetics," *Methods in Enzymology*, vol. 112, pp. 309-323 (1985).
Bodor, N., "Novel Approaches in Prodrug Design," *Drugs of the Future*, vol. 6, pp. 165-182 (1981).
Cao, et al., "TRPV1 Structures in Distinct Conformations Reveal Activation mechanisms," *Nature*, vol. 504, pp. 113-118 (2013).
Liao et al., "Structure of the TRPV1 ion channel determined by electron cryo-microscopy," *Nature*, vol. 504, pp. 107-111 (2013).

* cited by examiner

*Primary Examiner* — Golam M Shameem
(74) *Attorney, Agent, or Firm* — Foley & Lardner LLP

(57) ABSTRACT

Novel diphenylurea and benzylbenzenesulfonamide compounds are disclosed along with methods of inhibiting the activity of TRPV1 and methods of treating pain associated with transient receptor potential vanilloid type 1 (TRPV1) using such compounds.

8 Claims, 20 Drawing Sheets
Specification includes a Sequence Listing.

| ΔG | ID | 1 | 2 | 4 | 5 | 11 | 13 | 14 | 15 | 16 | 17 | 18 |
|---|---|---|---|---|---|---|---|---|---|---|---|---|
| | ΔG$_{actual}$ | - | - | - | - | -7.71 | -7.71 | -8.98 | -8.96 | -8.88 | -8.05 | -7.32 |
| | ΔG$_{predicted}$ | 7.94 | 7.59 | 7.00 | 7.87 | -6.55 | -6.96 | -7.68 | -7.94 | -8.46 | -6.51 | -6.10 |
| | | 7.70 | 5.81 | 6.12 | 6.70 | | | | | | | |

SEQUENCE LISTING

<160> NUMBER OF SEQ ID NOS: 2

<210> SEQ ID NO 1
<211> LENGTH: 839
<212> TYPE: PRT
<213> ORGANISM: Homo sapiens

<400> SEQUENCE: 1

```
Met Lys Lys Trp Ser Ser Thr Asp Leu Gly Ala Ala Ala Asp Pro Leu
1               5                   10                  15

Gln Lys Asp Thr Cys Pro Asp Pro Leu Asp Gly Asp Pro Asn Ser Arg
            20                  25                  30

Pro Pro Pro Ala Lys Pro Gln Leu Ser Thr Ala Lys Ser Arg Thr Arg
        35                  40                  45

Leu Phe Gly Lys Gly Asp Ser Glu Glu Ala Phe Pro Val Asp Cys Pro
    50                  55                  60

His Glu Glu Gly Glu Leu Asp Ser Cys Pro Thr Ile Thr Val Ser Pro
65                  70                  75                  80

Val Ile Thr Ile Gln Arg Pro Gly Asp Gly Pro Thr Gly Ala Arg Leu
                85                  90                  95

Leu Ser Gln Asp Ser Val Ala Ala Ser Thr Glu Lys Thr Leu Arg Leu
            100                 105                 110

Tyr Asp Arg Arg Ser Ile Phe Glu Ala Val Ala Gln Asn Asn Cys Gln
        115                 120                 125
```

-continued

```
Asp Leu Glu Ser Leu Leu Phe Leu Gln Lys Ser Lys Lys His Leu
    130                 135                 140

Thr Asp Asn Glu Phe Lys Asp Pro Glu Thr Gly Lys Thr Cys Leu Leu
145                 150                 155                 160

Lys Ala Met Leu Asn Leu His Asp Gly Gln Asn Thr Thr Ile Pro Leu
                165                 170                 175

Leu Leu Glu Ile Ala Arg Gln Thr Asp Ser Leu Lys Glu Leu Val Asn
            180                 185                 190

Ala Ser Tyr Thr Asp Ser Tyr Tyr Lys Gly Gln Thr Ala Leu His Ile
        195                 200                 205

Ala Ile Glu Arg Arg Asn Met Ala Leu Val Thr Leu Leu Val Glu Asn
210                 215                 220

Gly Ala Asp Val Gln Ala Ala His Gly Asp Phe Phe Lys Lys Thr
225                 230                 235                 240

Lys Gly Arg Pro Gly Phe Tyr Phe Gly Glu Leu Pro Leu Ser Leu Ala
                245                 250                 255

Ala Cys Thr Asn Gln Leu Gly Ile Val Lys Phe Leu Leu Gln Asn Ser
            260                 265                 270

Trp Gln Thr Ala Asp Ile Ser Ala Arg Asp Ser Val Gly Asn Thr Val
        275                 280                 285

Leu His Ala Leu Val Glu Val Ala Asp Asn Thr Ala Asp Asn Thr Lys
290                 295                 300

Phe Val Thr Ser Met Tyr Asn Glu Ile Leu Met Leu Gly Ala Lys Leu
305                 310                 315                 320

His Pro Thr Leu Lys Leu Glu Glu Leu Thr Asn Lys Lys Gly Met Thr
                325                 330                 335

Pro Leu Ala Leu Ala Ala Gly Thr Gly Lys Ile Gly Val Leu Ala Tyr
            340                 345                 350

Ile Leu Gln Arg Glu Ile Gln Glu Pro Glu Cys Arg His Leu Ser Arg
        355                 360                 365

Lys Phe Thr Glu Trp Ala Tyr Gly Pro Val His Ser Ser Leu Tyr Asp
370                 375                 380

Leu Ser Cys Ile Asp Thr Cys Glu Lys Asn Ser Val Leu Glu Val Ile
385                 390                 395                 400

Ala Tyr Ser Ser Ser Glu Thr Pro Asn Arg His Asp Met Leu Leu Val
                405                 410                 415

Glu Pro Leu Asn Arg Leu Leu Gln Asp Lys Trp Asp Arg Phe Val Lys
            420                 425                 430

Arg Ile Phe Tyr Phe Asn Phe Leu Val Tyr Cys Leu Tyr Met Ile Ile
        435                 440                 445

Phe Thr Met Ala Ala Tyr Tyr Arg Pro Val Asp Gly Leu Pro Pro Phe
450                 455                 460

Lys Met Glu Lys Thr Gly Asp Tyr Phe Arg Val Thr Gly Glu Ile Leu
465                 470                 475                 480

Ser Val Leu Gly Gly Val Tyr Phe Phe Phe Arg Gly Ile Gln Tyr Phe
                485                 490                 495

Leu Gln Arg Arg Pro Ser Met Lys Thr Leu Phe Val Asp Ser Tyr Ser
            500                 505                 510

Glu Met Leu Phe Phe Leu Gln Ser Leu Phe Met Leu Ala Thr Val Val
        515                 520                 525

Leu Tyr Phe Ser His Leu Lys Glu Tyr Val Ala Ser Met Val Phe Ser
530                 535                 540
```

```
Leu Ala Leu Gly Trp Thr Asn Met Leu Tyr Tyr Thr Arg Gly Phe Gln
545                 550                 555                 560

Gln Met Gly Ile Tyr Ala Val Met Ile Glu Lys Met Ile Leu Arg Asp
            565                 570                 575

Leu Cys Arg Phe Met Phe Val Tyr Ile Val Phe Leu Phe Gly Phe Ser
        580                 585                 590

Thr Ala Val Val Thr Leu Ile Glu Asp Gly Lys Asn Asp Ser Leu Pro
    595                 600                 605

Ser Glu Ser Thr Ser His Arg Trp Arg Gly Pro Ala Cys Arg Pro Pro
610                 615                 620

Asp Ser Ser Tyr Asn Ser Leu Tyr Ser Thr Cys Leu Glu Leu Phe Lys
625                 630                 635                 640

Phe Thr Ile Gly Met Gly Asp Leu Glu Phe Thr Glu Asn Tyr Asp Phe
                645                 650                 655

Lys Ala Val Phe Ile Ile Leu Leu Leu Ala Tyr Val Ile Leu Thr Tyr
            660                 665                 670

Ile Leu Leu Leu Asn Met Leu Ile Ala Leu Met Gly Glu Thr Val Asn
            675                 680                 685

Lys Ile Ala Gln Glu Ser Lys Asn Ile Trp Lys Leu Gln Arg Ala Ile
690                 695                 700

Thr Ile Leu Asp Thr Glu Lys Ser Phe Leu Lys Cys Met Arg Lys Ala
705                 710                 715                 720

Phe Arg Ser Gly Lys Leu Leu Gln Val Gly Tyr Thr Pro Asp Gly Lys
                725                 730                 735

Asp Asp Tyr Arg Trp Cys Phe Arg Val Asp Glu Val Asn Trp Thr Thr
            740                 745                 750

Trp Asn Thr Asn Val Gly Ile Ile Asn Glu Asp Pro Gly Asn Cys Glu
            755                 760                 765

Gly Val Lys Arg Thr Leu Ser Phe Ser Leu Arg Ser Ser Arg Val Ser
770                 775                 780

Gly Arg His Trp Lys Asn Phe Ala Leu Val Pro Leu Leu Arg Glu Ala
785                 790                 795                 800

Ser Ala Arg Asp Arg Gln Ser Ala Gln Pro Glu Glu Val Tyr Leu Arg
                805                 810                 815

Gln Phe Ser Gly Ser Leu Lys Pro Glu Asp Ala Glu Val Phe Lys Ser
                820                 825                 830

Pro Ala Ala Ser Gly Glu Lys
            835

<210> SEQ ID NO 2
<211> LENGTH: 838
<212> TYPE: PRT
<213> ORGANISM: Rattus norvegicus

<400> SEQUENCE: 2

Met Glu Gln Arg Ala Ser Leu Asp Ser Glu Glu Ser Glu Ser Pro Pro
1               5                   10                  15

Gln Glu Asn Ser Cys Leu Asp Pro Pro Asp Arg Asp Pro Asn Cys Lys
            20                  25                  30

Pro Pro Pro Val Lys Pro His Ile Phe Thr Thr Arg Ser Arg Thr Arg
        35                  40                  45

Leu Phe Gly Lys Gly Asp Ser Glu Ala Ser Pro Leu Asp Cys Pro
    50                  55                  60

Tyr Glu Glu Gly Gly Leu Ala Ser Cys Pro Ile Ile Thr Val Ser Ser
65                  70                  75                  80
```

```
Val Leu Thr Ile Gln Arg Pro Gly Asp Gly Pro Ala Ser Val Arg Pro
             85                  90                  95

Ser Ser Gln Asp Ser Val Ser Ala Gly Glu Lys Pro Pro Arg Leu Tyr
        100                 105                 110

Asp Arg Arg Ser Ile Phe Asp Ala Val Ala Gln Ser Asn Cys Gln Glu
            115                 120                 125

Leu Glu Ser Leu Leu Pro Phe Leu Gln Arg Ser Lys Lys Arg Leu Thr
130                 135                 140

Asp Ser Glu Phe Lys Asp Pro Glu Thr Gly Lys Thr Cys Leu Leu Lys
145                 150                 155                 160

Ala Met Leu Asn Leu His Asn Gly Gln Asn Asp Thr Ile Ala Leu Leu
                165                 170                 175

Leu Asp Val Ala Arg Lys Thr Asp Ser Leu Lys Gln Phe Val Asn Ala
            180                 185                 190

Ser Tyr Thr Asp Ser Tyr Tyr Lys Gly Gln Thr Ala Leu His Ile Ala
        195                 200                 205

Ile Glu Arg Arg Asn Met Thr Leu Val Thr Leu Leu Val Glu Asn Gly
    210                 215                 220

Ala Asp Val Gln Ala Ala Ala Asn Gly Asp Phe Phe Lys Lys Thr Lys
225                 230                 235                 240

Gly Arg Pro Gly Phe Tyr Phe Gly Glu Leu Pro Leu Ser Leu Ala Ala
                245                 250                 255

Cys Thr Asn Gln Leu Ala Ile Val Lys Phe Leu Leu Gln Asn Ser Trp
            260                 265                 270

Gln Pro Ala Asp Ile Ser Ala Arg Asp Ser Val Gly Asn Thr Val Leu
        275                 280                 285

His Ala Leu Val Glu Val Ala Asp Asn Thr Val Asp Asn Thr Lys Phe
    290                 295                 300

Val Thr Ser Met Tyr Asn Glu Ile Leu Ile Leu Gly Ala Lys Leu His
305                 310                 315                 320

Pro Thr Leu Lys Leu Glu Glu Ile Thr Asn Arg Lys Gly Leu Thr Pro
                325                 330                 335

Leu Ala Leu Ala Ala Ser Ser Gly Lys Ile Gly Val Leu Ala Tyr Ile
            340                 345                 350

Leu Gln Arg Glu Ile His Glu Pro Glu Cys Arg His Leu Ser Arg Lys
        355                 360                 365

Phe Thr Glu Trp Ala Tyr Gly Pro Val His Ser Ser Leu Tyr Asp Leu
    370                 375                 380

Ser Cys Ile Asp Thr Cys Glu Lys Asn Ser Val Leu Glu Val Ile Ala
385                 390                 395                 400

Tyr Ser Ser Ser Glu Thr Pro Asn Arg His Asp Met Leu Leu Val Glu
                405                 410                 415

Pro Leu Asn Arg Leu Leu Gln Asp Lys Trp Asp Arg Phe Val Lys Arg
            420                 425                 430

Ile Phe Tyr Phe Asn Phe Phe Val Tyr Cys Leu Tyr Met Ile Ile Phe
        435                 440                 445

Thr Ala Ala Ala Tyr Tyr Arg Pro Val Glu Gly Leu Pro Pro Tyr Lys
    450                 455                 460

Leu Lys Asn Thr Val Gly Asp Tyr Phe Arg Val Thr Gly Glu Ile Leu
465                 470                 475                 480

Ser Val Ser Gly Gly Val Tyr Phe Phe Phe Arg Gly Ile Gln Tyr Phe
                485                 490                 495
```

```
Leu Gln Arg Arg Pro Ser Leu Lys Ser Leu Phe Val Asp Ser Tyr Ser
            500                 505                 510
Glu Ile Leu Phe Phe Val Gln Ser Leu Phe Met Leu Val Ser Val Val
            515                 520                 525
Leu Tyr Phe Ser Gln Arg Lys Glu Tyr Val Ala Ser Met Val Phe Ser
            530                 535                 540
Leu Ala Met Gly Trp Thr Asn Met Leu Tyr Tyr Thr Arg Gly Phe Gln
545                 550                 555                 560
Gln Met Gly Ile Tyr Ala Val Met Ile Glu Lys Met Ile Leu Arg Asp
                565                 570                 575
Leu Cys Arg Phe Met Phe Val Tyr Leu Val Phe Leu Phe Gly Phe Ser
                580                 585                 590
Thr Ala Val Val Thr Leu Ile Glu Asp Gly Lys Asn Asn Ser Leu Pro
                595                 600                 605
Met Glu Ser Thr Pro His Lys Cys Arg Gly Ser Ala Cys Lys Pro Gly
                610                 615                 620
Asn Ser Tyr Asn Ser Leu Tyr Ser Thr Cys Leu Glu Leu Phe Lys Phe
625                 630                 635                 640
Thr Ile Gly Met Gly Asp Leu Glu Phe Thr Glu Asn Tyr Asp Phe Lys
                645                 650                 655
Ala Val Phe Ile Ile Leu Leu Leu Ala Tyr Val Ile Leu Thr Tyr Ile
                660                 665                 670
Leu Leu Leu Asn Met Leu Ile Ala Leu Met Gly Glu Thr Val Asn Lys
                675                 680                 685
Ile Ala Gln Glu Ser Lys Asn Ile Trp Lys Leu Gln Arg Ala Ile Thr
            690                 695                 700
Ile Leu Asp Thr Glu Lys Ser Phe Leu Lys Cys Met Arg Lys Ala Phe
705                 710                 715                 720
Arg Ser Gly Lys Leu Leu Gln Val Gly Phe Thr Pro Asp Gly Lys Asp
                725                 730                 735
Asp Tyr Arg Trp Cys Phe Arg Val Asp Glu Val Asn Trp Thr Thr Trp
                740                 745                 750
Asn Thr Asn Val Gly Ile Ile Asn Glu Asp Pro Gly Asn Cys Glu Gly
                755                 760                 765
Val Lys Arg Thr Leu Ser Phe Ser Leu Arg Ser Gly Arg Val Ser Gly
            770                 775                 780
Arg Asn Trp Lys Asn Phe Ala Leu Val Pro Leu Leu Arg Asp Ala Ser
785                 790                 795                 800
Thr Arg Asp Arg His Ala Thr Gln Gln Glu Glu Val Gln Leu Lys His
                805                 810                 815
Tyr Thr Gly Ser Leu Lys Pro Glu Asp Ala Glu Val Phe Lys Asp Ser
            820                 825                 830
Met Val Pro Gly Glu Lys
            835
```

HTRPVI CHEMICAL AGENTS

CROSS REFERENCE TO RELATED APPLICATIONS

The present application is the U.S. National Stage of International Patent Application No. PCT/US2016/016826, filed Feb. 5, 2016, which claims priority from U.S. Provisional Patent Application No. 62/113,429, filed Feb. 7, 2015. The contents of these applications are incorporated herein by reference in their entirety.

STATEMENT OF GOVERNMENT SUPPORT

This invention was made with government support under NIH grant #DA025612 awarded by the NIH. The government has certain rights in the invention.

SEQUENCE LISTING

The instant application contains a Sequence Listing which has been submitted electronically in ASCII format and is hereby incorporated by reference in its entirety. Said ASCII copy, created on Dec. 4, 2017, is named 076333-0897_SL.txt and is 14,752 bytes in size.

BACKGROUND

Transient receptor potential (TRP) channels are among the largest families of ion channels. There are 28 known TRP cation channels in the TRP superfamily, which can be further subdivided into six subfamilies: TRPA ("Ankyrin": TRPA1), TRPML ("Mucolipin": TRPML1-TRPML3), TRPP ("Polycystin": TRPP1-TRPP3), TRPM ("Melastatin": TRPM1-TRPM8), TRPC ("Canonical":TRPC1-TRPC7), and TRPV ("Vanilloid": TRPV1-TRPV6).

Transient receptor potential vanilloid type 1 (TRPV1) is a member of the TRPV subfamily. TRPV1 and has been reported to contribute to acute and chronic pain, such as osteoarthritis, neuropathic pain, migraine, inflammatory bowel disease, and bone cancer pain. Brain TRPV1 is also postulated to have a pathogenic role in various neurological and psychiatric disorders, ranging from Parkinson's disease, schizophrenia, and Alzheimer disease to anxiety, depression and other mood disorders.

Recently, the structures of *Rattus norvegicus* apo-TRPV1 (rTRPV1), rTRPV1 bound with RTX/DkTx or with capsaicin has been reported by using single particle electron cryo-microscopy. Cao et al., "TRPV1 Structures in Distinct Conformations Reveal Activation Mechanisms," Nature, 504:113-118 (2013); Liao et al., "Structure of the TRPV1 Ion Channel Determined by Electron Cryo-Microscopy," Nature, 504:107-11 (2013). Unfortunately, the resolution was insufficient to reveal in detail the nature of the ligand binding interactions with TRPV1.

Human TRPV1 (hTRPV1) shares 85.7% sequence identity with rTRPV1. Most of the antagonists of hTRPV1, which represent the predominant therapeutic strategy for utilization of vanilloids in the treatment of pain, share a scaffold and R-groups. Developing antagonists of hTRPV1 has been hindered by the unavailability of the 3D structure of hTRPV1.

Thus, there remains a need in the art to determine a pharmacophore model of hTRPV1. Furthermore, there remains a need in the art to develop new antagonists for hTRPV1.

SUMMARY OF THE INVENTION

One embodiment of the invention relates to a compound represented by Formula (I):

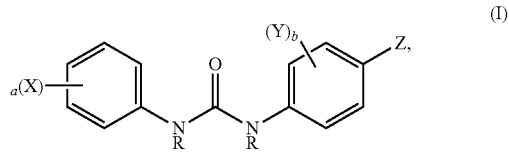

wherein:

X is independently in each instance halogen, OH, amino, COOH, $CONH_2$, $SO_3H$, $PO_3H_2$, CN, SH, $N(R')_2$, $NO_2$, $CF_3C_1-C_6$ perfluoroalkyl, NHC(O)—$C_1$-$C_6$ alkyl, NHC(O)—$C_1$-$C_6$ perfluoroalkyl, ($C_1$-$C_6$)alkyl, ($C_1$-$C_6$)alkoxy, ($C_1$-$C_6$)haloalkoxy, ($C_1$-$C_6$)haloalkyl, ($C_2$-$C_6$)alkenyl, ($C_2$-$C_6$)alkynyl, —$NH_2$, —NH($C_1$-$C_6$)alkyl, —N[($C_1$-$C_6$)alkyl]$_2$, —CN, ($C_3$-$C_8$)heteroaryl, ($C_3$-$C_8$)heterocycloalkyl, ($C_3$-$C_8$)cycloalkyl, ($C_3$-$C_8$)aryl, ($C_3$-$C_8$)heterocycloalkyl-($C_1$-$C_6$)alkylene-, ($C_3$-$C_8$)heteroaryl-($C_1$-$C_6$)alkylene-, ($C_3$-$C_8$)aryl($C_1$-$C_6$)alkylene-, ($C_3$-$C_8$)aryl($C_1$-$C_6$)alkenylene-, or ($C_1$-$C_6$)alkyl-($C_3$-$C_8$)arylene; Y is independently in each instance halogen, OH, amino, COOH, $CONH_2$, $SO_3H$, $PO_3H_2$, CN, SH, $N(R')_2$, $NO_2$, $CF_3C_1-C_6$ perfluoroalkyl, NHC(O)—$C_1$-$C_6$ alkyl, NHC(O)—$C_1$-$C_6$ perfluoroalkyl, ($C_1$-$C_6$)alkyl, ($C_1$-$C_6$)alkoxy, ($C_1$-$C_6$)haloalkoxy, ($C_1$-$C_6$)haloalkyl, ($C_2$-$C_6$)alkenyl, ($C_2$-$C_6$)alkynyl, —$NH_2$, —NH($C_1$-$C_6$)alkyl, —N[($C_1$-$C_6$)alkyl]$_2$, —CN, ($C_3$-$C_8$)heteroaryl, ($C_3$-$C_8$)heterocycloalkyl, ($C_3$-$C_8$)cycloalkyl, ($C_3$-$C_8$)aryl, ($C_3$-$C_8$)heterocycloalkyl-($C_1$-$C_6$)alkylene-, ($C_3$-$C_8$)heteroaryl-($C_1$-$C_6$)alkylene-, ($C_3$-$C_8$)aryl($C_1$-$C_6$)alkylene-, ($C_3$-$C_8$)aryl($C_1$-$C_6$)alkenylene-, or ($C_1$-$C_6$)alkyl-($C_3$-$C_8$)arylene; Z is halogen, OH, amino, COOH, $CONH_2$, $SO_3H$, $PO_3H_2$, CN, SH, $N(R')_2$, $NO_2$, $CF_3C_1-C_6$ perfluoroalkyl, NHC(O)—$C_1$-$C_6$ alkyl, NHC(O)—$C_1$-$C_6$ perfluoroalkyl, ($C_1$-$C_6$)alkyl, ($C_1$-$C_6$)alkoxy, ($C_1$-$C_6$)haloalkoxy, ($C_1$-$C_6$)haloalkyl, ($C_2$-$C_6$)alkenyl, ($C_2$-$C_6$)alkynyl, —$NH_2$, —NH($C_1$-$C_6$)alkyl, —N[($C_1$-$C_6$)alkyl]$_2$, —CN, ($C_3$-$C_8$)heteroaryl, ($C_3$-$C_8$)heterocycloalkyl, ($C_3$-$C_8$)cycloalkyl, ($C_3$-$C_8$)aryl, ($C_3$-$C_8$)heterocycloalkyl-($C_1$-$C_6$)alkylene-, ($C_3$-$C_8$)heteroaryl-($C_1$-$C_6$)alkylene-, ($C_3$-$C_8$)aryl($C_1$-$C_6$)alkylene-, ($C_3$-$C_8$)aryl($C_1$-$C_6$)alkenylene-, or ($C_1$-$C_6$)alkyl-($C_3$-$C_8$)arylene; R is independently in each instance H, —OH, ($C_1$-$C_6$)alkyl, ($C_1$-$C_6$) perfluoroalkyl; ($C_1$-$C_6$)alkoxy, ($C_1$-$C_6$)haloalkoxy, ($C_1$-$C_6$)haloalkyl, ($C_2$-$C_6$)alkenyl, ($C_2$-$C_6$)alkynyl, —$NH_2$, —NH($C_1$-$C_6$)alkyl, —N[($C_1$-$C_6$)alkyl]$_2$, —CN, ($C_3$-$C_8$)heteroaryl, ($C_3$-$C_8$)heterocycloalkyl, ($C_3$-$C_8$)cycloalkyl, ($C_3$-$C_8$)aryl, ($C_3$-$C_8$)heterocycloalkyl-($C_1$-$C_6$)alkylene-, ($C_3$-$C_8$)heteroaryl-($C_1$-$C_6$)alkylene-, ($C_3$-$C_8$)aryl($C_1$-$C_6$)alkylene-, ($C_3$-$C_8$)aryl($C_1$-$C_6$)alkenylene-, or ($C_1$-$C_6$)alkyl-($C_3$-$C_8$)arylene; R' is independently in each instance H, —OH, ($C_1$-$C_6$)alkyl, ($C_1$-$C_6$) perfluoroalkyl; ($C_1$-$C_6$)alkoxy, ($C_1$-$C_6$)haloalkoxy, ($C_1$-$C_6$)haloalkyl, ($C_2$-$C_6$)alkenyl, ($C_2$-$C_6$)alkynyl, —$NH_2$, —NH($C_1$-$C_6$)alkyl, —N[($C_1$-$C_6$)alkyl]$_2$, —CN, ($C_3$-$C_8$)heteroaryl, ($C_3$-$C_8$)heterocycloalkyl, ($C_3$-$C_8$)cycloalkyl, ($C_3$-$C_8$)aryl, ($C_3$-$C_8$)heterocycloalkyl-($C_1$-$C_6$)alkylene-, ($C_3$-$C_8$)heteroaryl-($C_1$-$C_6$)alkylene-, ($C_3$-$C_8$)aryl($C_1$-$C_6$)alkylene-, ($C_3$-$C_8$)aryl($C_1$-$C_6$)alkenylene-, or ($C_1$-$C_6$)alkyl-($C_3$-$C_8$)arylene; a is an integer of 0 to 5; and b is an integer of 0 to 4, wherein the alkyl moieties are optionally substituted by one or more halogen, or a pharmaceutically acceptable salt or solvate thereof.

In another embodiment, Z is N(R')$_2$ or NO$_2$ and a is an integer of 1 to 5; and b is an integer of 0 to 4. In yet another embodiment, X is independently in each instance halogen, C$_1$-C$_6$ alkyl, C$_1$-C$_6$ perfluoroalkyl, NHC(O)—C$_1$-C$_6$ alkyl, NHC(O)—C$_1$-C$_6$ perfluoroalkyl; Y is independently in each instance halogen, C$_1$-C$_6$ alkyl; Z is N(R')$_2$, NO$_2$; R is independently in each instance H, C$_1$-C$_6$ alkyl; R' is independently in each instance H, C$_1$-C$_6$ alkyl, C$_1$-C$_6$ perfluoroalkyl; a is an integer of 1 to 5; and b is an integer of 0 to 4, wherein the alkyl moieties are optionally substituted by one or more halogen, or a pharmaceutically acceptable salt or solvate thereof.

In another embodiment, a and b are each independently an integer of 1 to 3, or a and b are one. In another embodiment, X is fluoro, C$_1$-C$_6$ alkyl or C$_1$-C$_6$ perfluoroalkyl and a is 1. In another embodiment, Y is a C$_1$-C$_6$ alkyl and b is 1. In another embodiment, R is H. In another embodiment, Z is NO$_2$.

Other aspects of the present invention include a pharmaceutical composition comprising a compound of any of the prior embodiments and at least one pharmaceutically acceptable carrier.

Another aspect of the present invention includes a method of treating pain associated with transient receptor potential vanilloid type 1 (TRPV1) in a subject in need thereof, comprising administering to the subject an effective amount of a compound or composition of any of the prior embodiments. In some embodiments, the pain associated with TRPV1 is selected from the group consisting of osteoarthritis, neuropathic pain, migraine, inflammatory bowel disease, and bone cancer pain.

Yet another aspect of the present invention includes a method of inhibiting the activity of TRPV1 comprising contacting TRPV1 with a compound or composition of any prior embodiments.

The foregoing general description and following description of the drawings and detailed description are exemplary and explanatory and are intended to provide further explanation of the invention as claimed. Other objects, advantages, and novel features will be readily apparent to those skilled in the art from the following brief description of the drawings and detailed description of the invention.

BRIEF DESCRIPTION OF THE DRAWINGS

Figure 1:
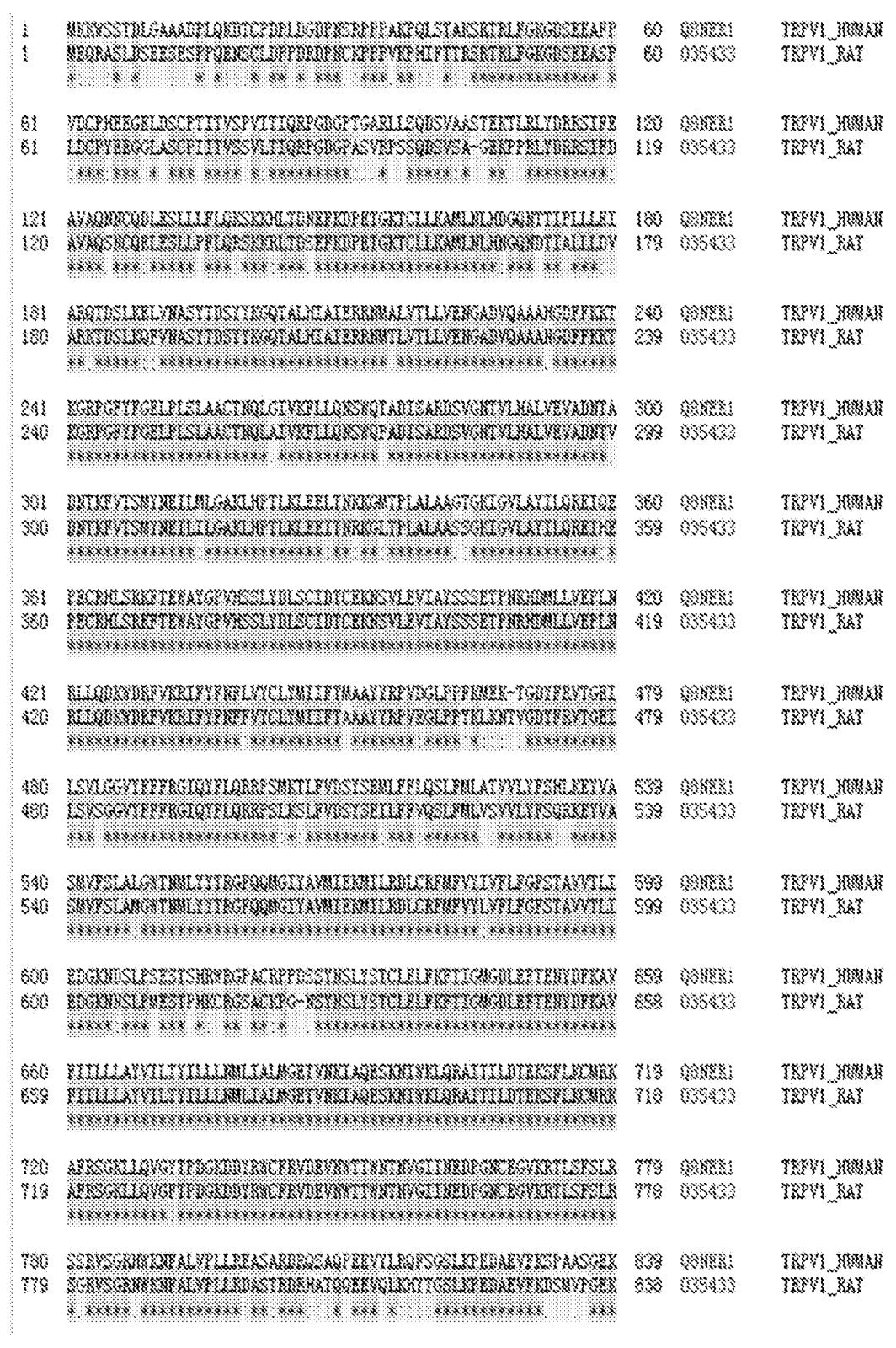

FIG. 1 is a sequence alignment between hTRPV1 (SEQ ID NO: 1) and rTRPV1 (SEQ ID NO: 2) in the present work.

FIG. 2A=General case; FIG. 2B=isoleucine and valine; FIG. 2C=pre-proline; FIG. 2D=glycine; FIG. 2E=trans proline; and FIG. 2F=cis proline. 95.5% (554/580) of all residues were in favored regions. 99.1% (575/580) of all residues were in allowed regions. There were 5 outliers (phi, psi): Glu250 (56.0, −24.3), Leu385 (88.0, 72.8), Thr407 (88.0, −19.7), Asp459 (22.4, −126.2), Pro462 (−28.9, −68.7).

DETAILED DESCRIPTION

Compounds of the Invention

Figure 2:
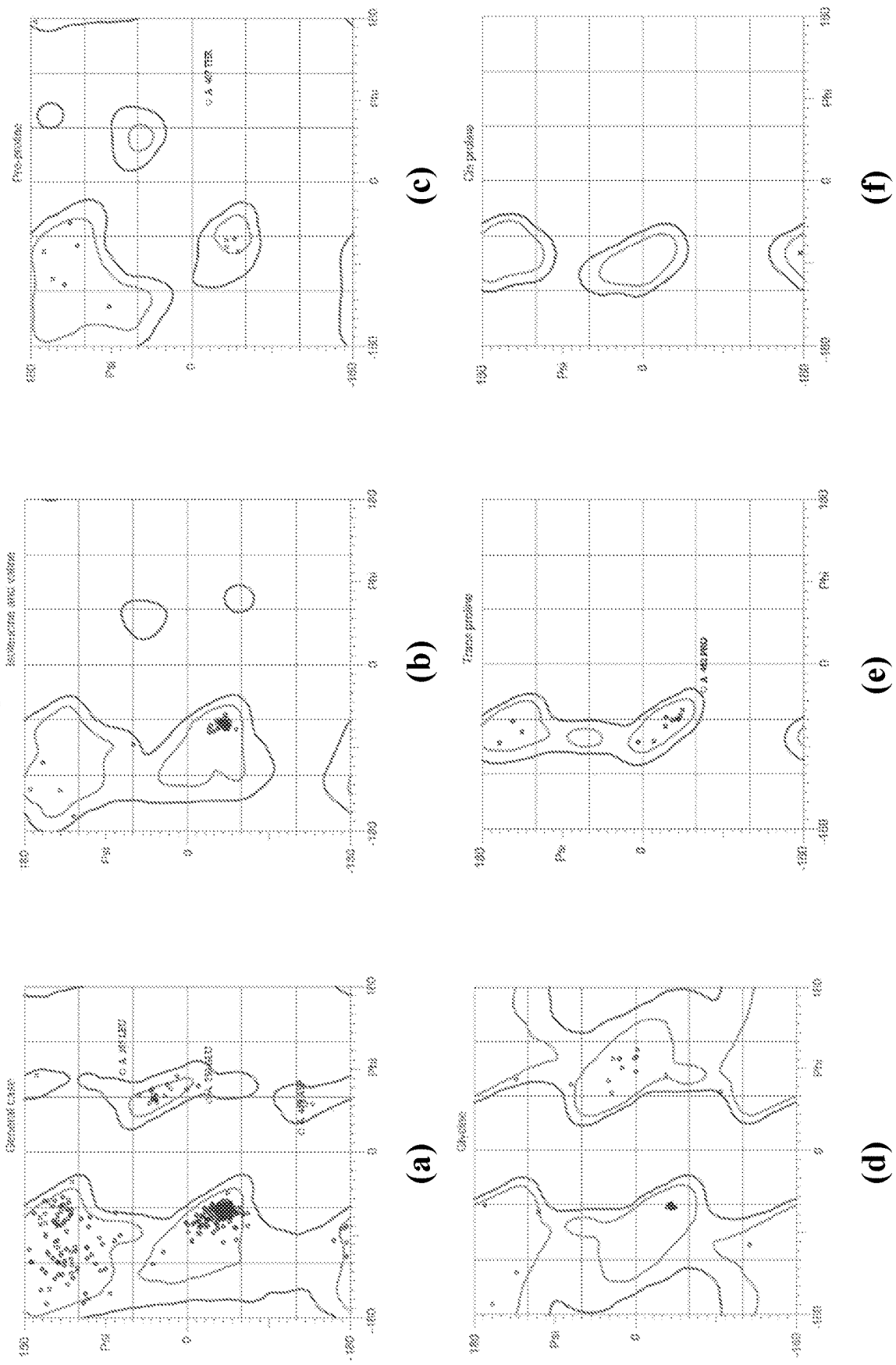
FIGS. 2A-2F are Ramachandran plots of hTRPV1 model constructed by rTRPV1.
Figure 3:
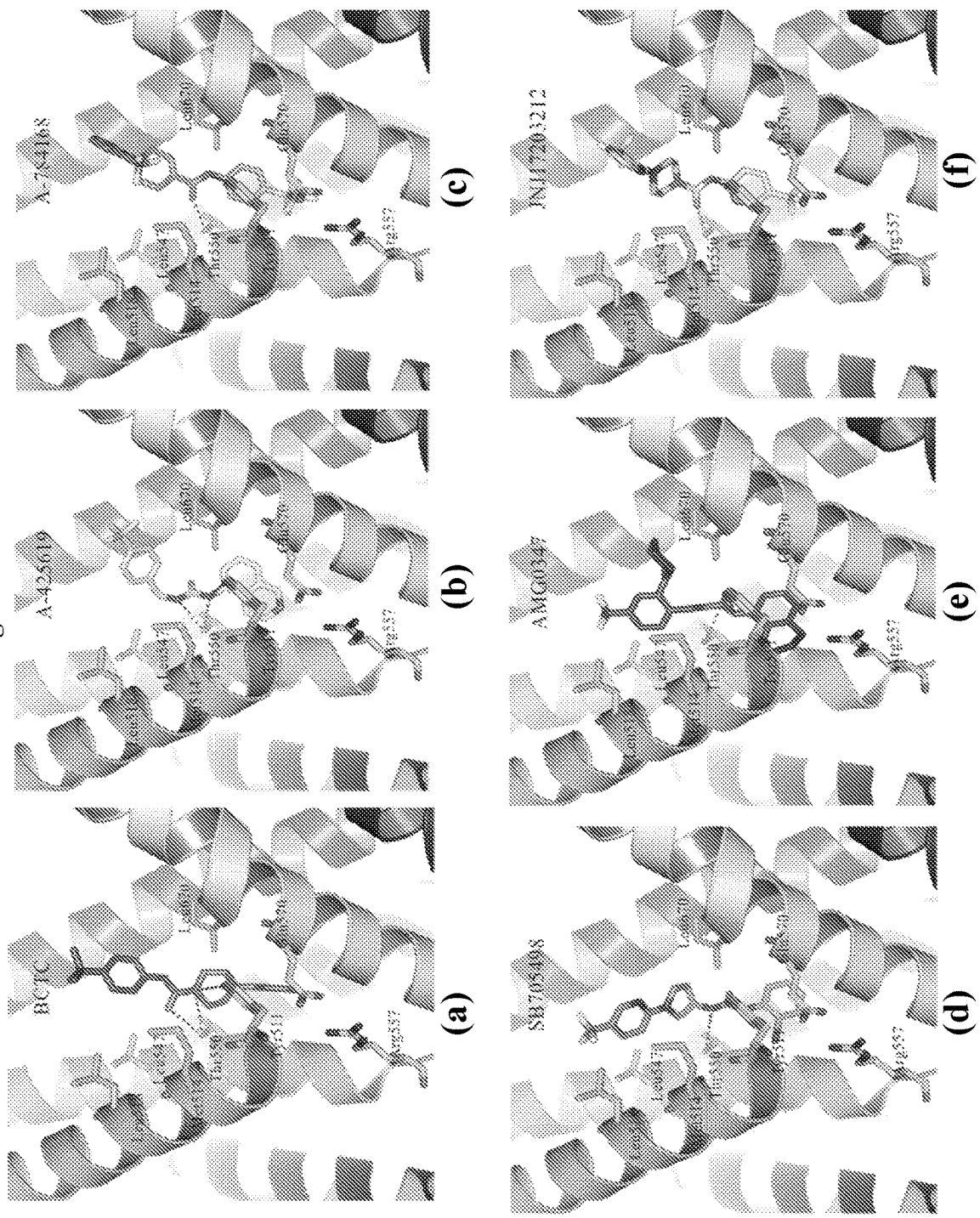
FIGS. 3A-3F show detailed binding modes of six other antagonists with hTRPV1, including BCTC (FIG. 3A), A-425619 (FIG. 3B), A-784168 (FIG. 3C), SB705498 (FIG. 3D), AMG0347 (FIG. 3E), and JNJ17203212 (FIG. 3F). Two residues, Tyr511 and Thr550, formed strong hydrogen bonds with the antagonists.
Figure 4:
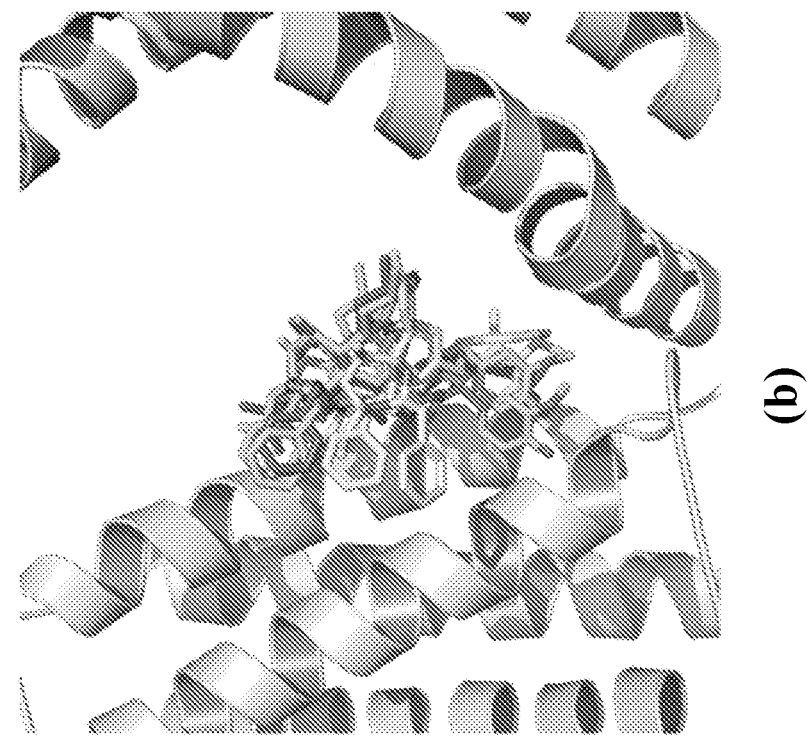
FIGS. 4A and 4B show alignments of (a) four AMG9810 and (b) of four RTX after MD simulation. The hTRPV1 and its compounds before MD simulation were highlighted in gray, while the four AMG9810 and four RTX in different monomers were highlighted in colors.
Figure 4:
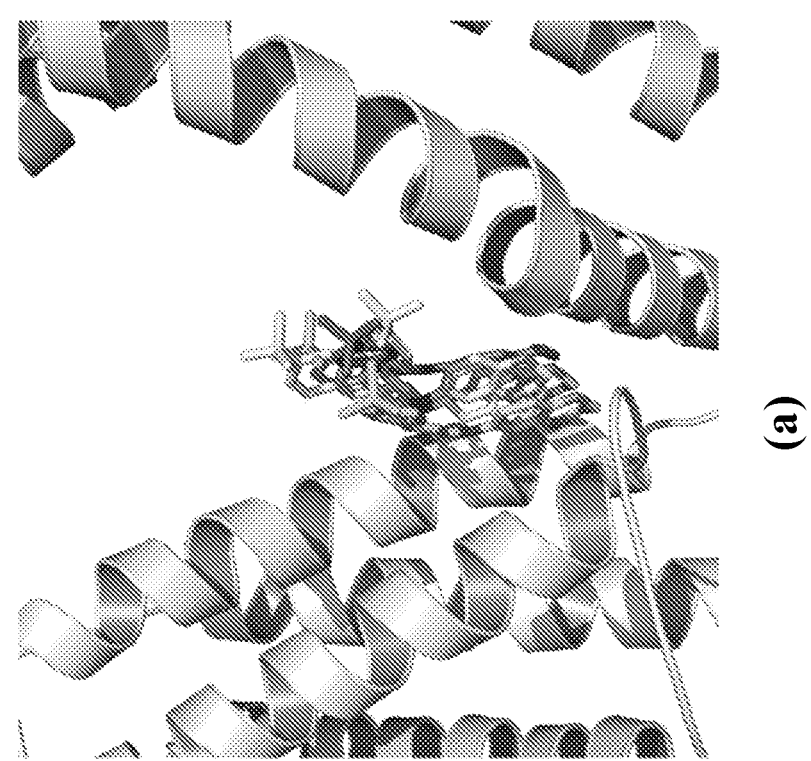
Figure 5:
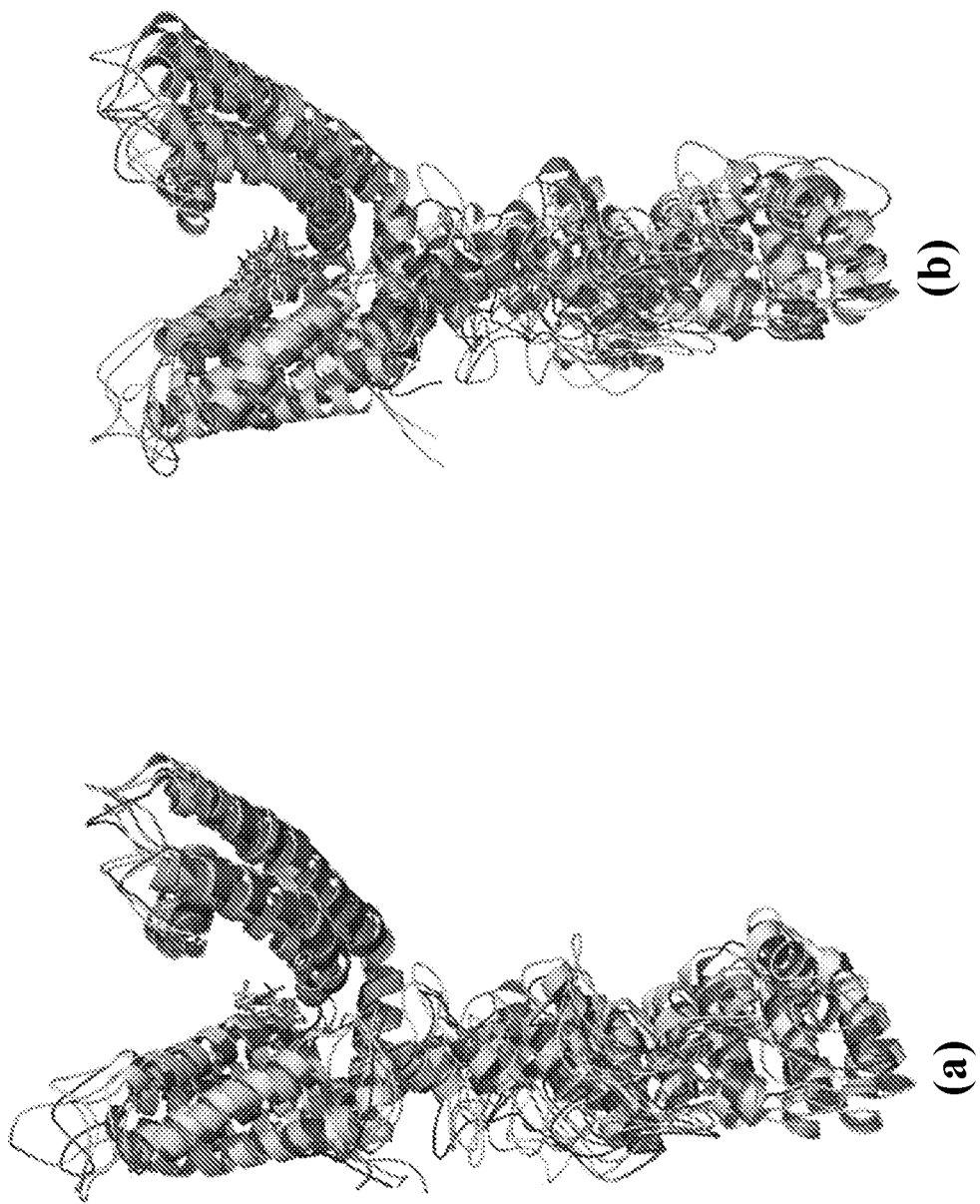
FIGS. 5A and 5B show alignments of four monomers (or units) (a) of hTRPV1 bound with AMG9810 and (b) of hTRPV1 bound with RTX.
Figure 6:
FIG. 6 is alignments of hTRPV1 bound with AMG9810 and bound with RTX. hTRPV1 highlighted in green color was the structure of hTRPV1 bound with antagonist, while hTRPV1 highlighted in red color was the structure of hTRPV1 bound with agonist. Residues from 112 to 364 were hindered for clarity.
Figure 7:
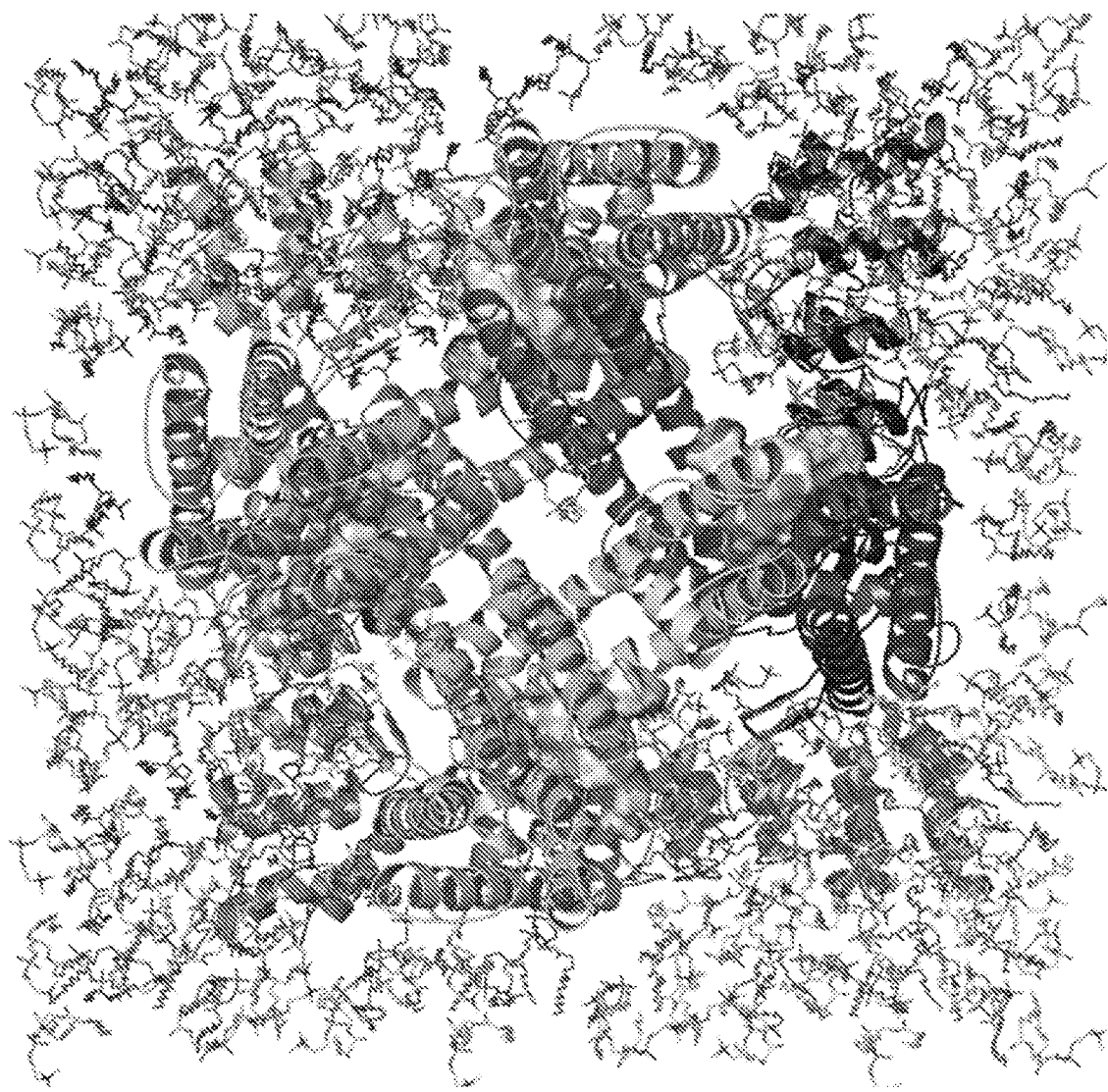
FIG. 7 shows four allosteric binding pockets in tetramer hTRPV1 model.
Figure 8:
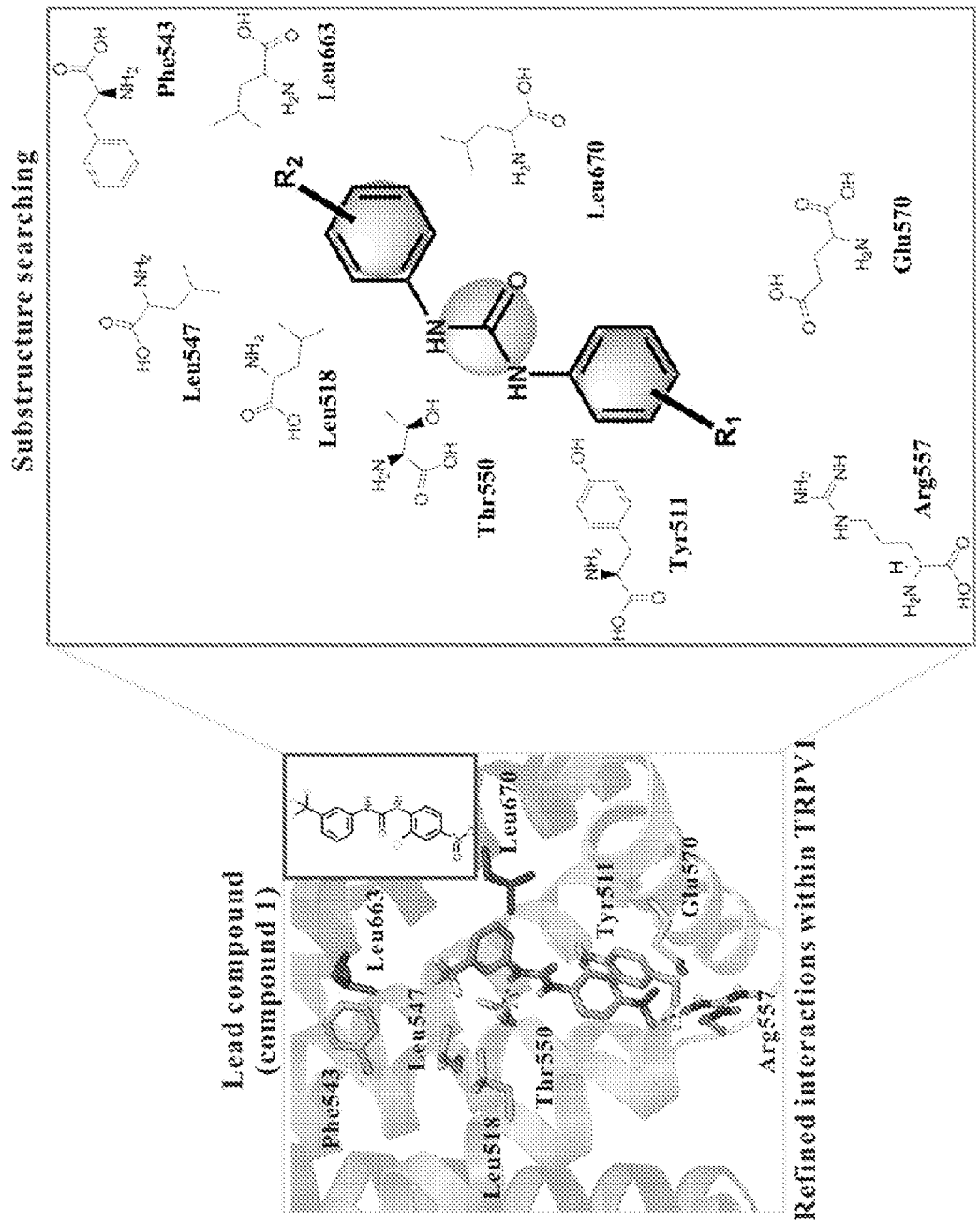
FIG. 8 shows a substructure search of diarylurea small molecules (derived from compound 1) against a refined compound library of 15,672 compounds for TRPV1.
Figure 9:
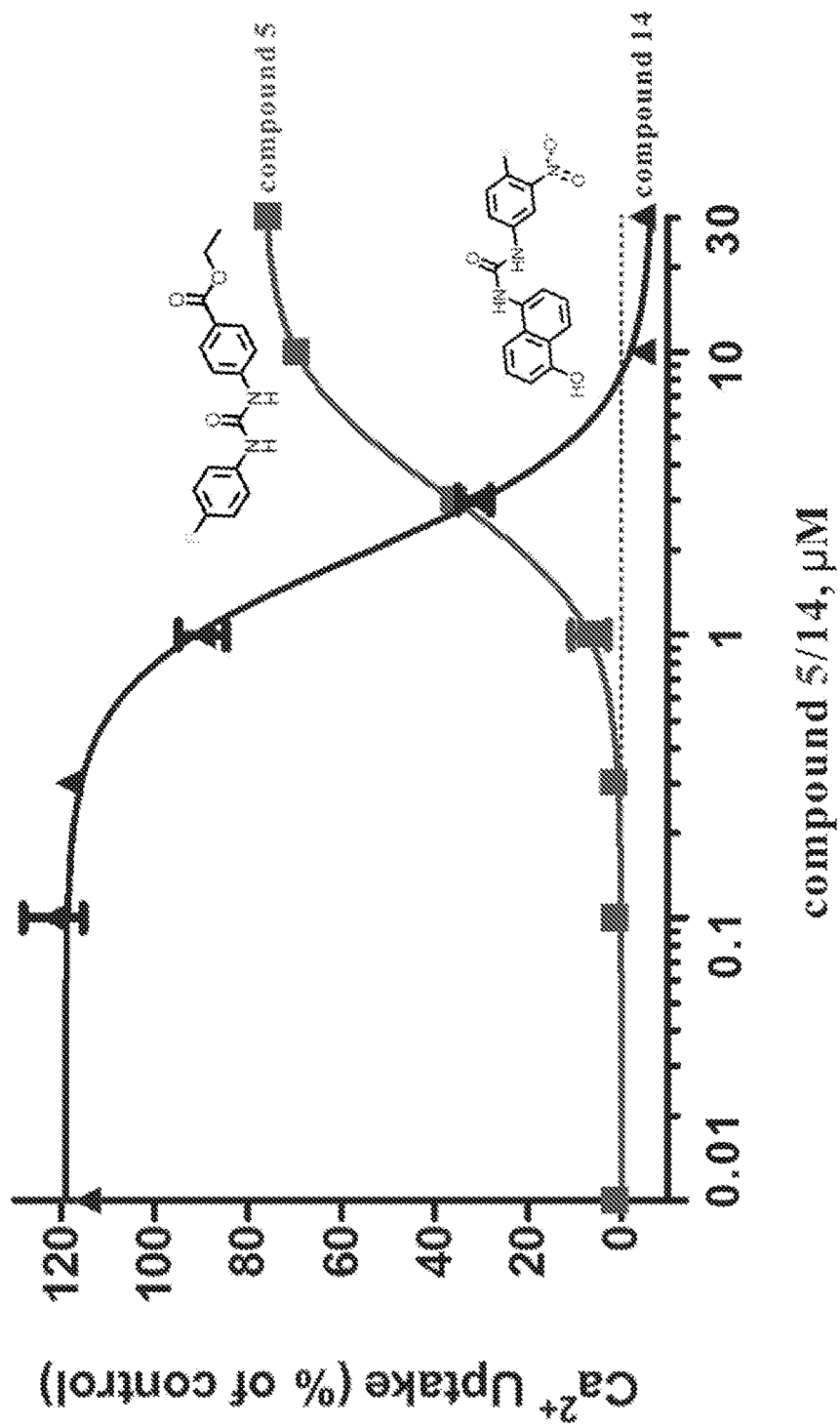
FIG. 9 shows chemical structures and activity values of compounds 5 and 14. Compound 5 (partial agonist) yielded an EC$_{50}$ value for capsaicin agonism of 2.84±0.21 μM and maximal stimulation 55.7±7.8% of that by 3000 nM capsaicin (FIG. 9, red line). Compound 14 (antagonist) yielded a K$_i$ value for capsaicin antagonism of 0.47±0.18 μM (FIG. 9, blue line) and inhibited [$^3$H]RTX binding to hTRPV1 with a K$_i$ value of 0.65±0.26 μM
Figure 10:
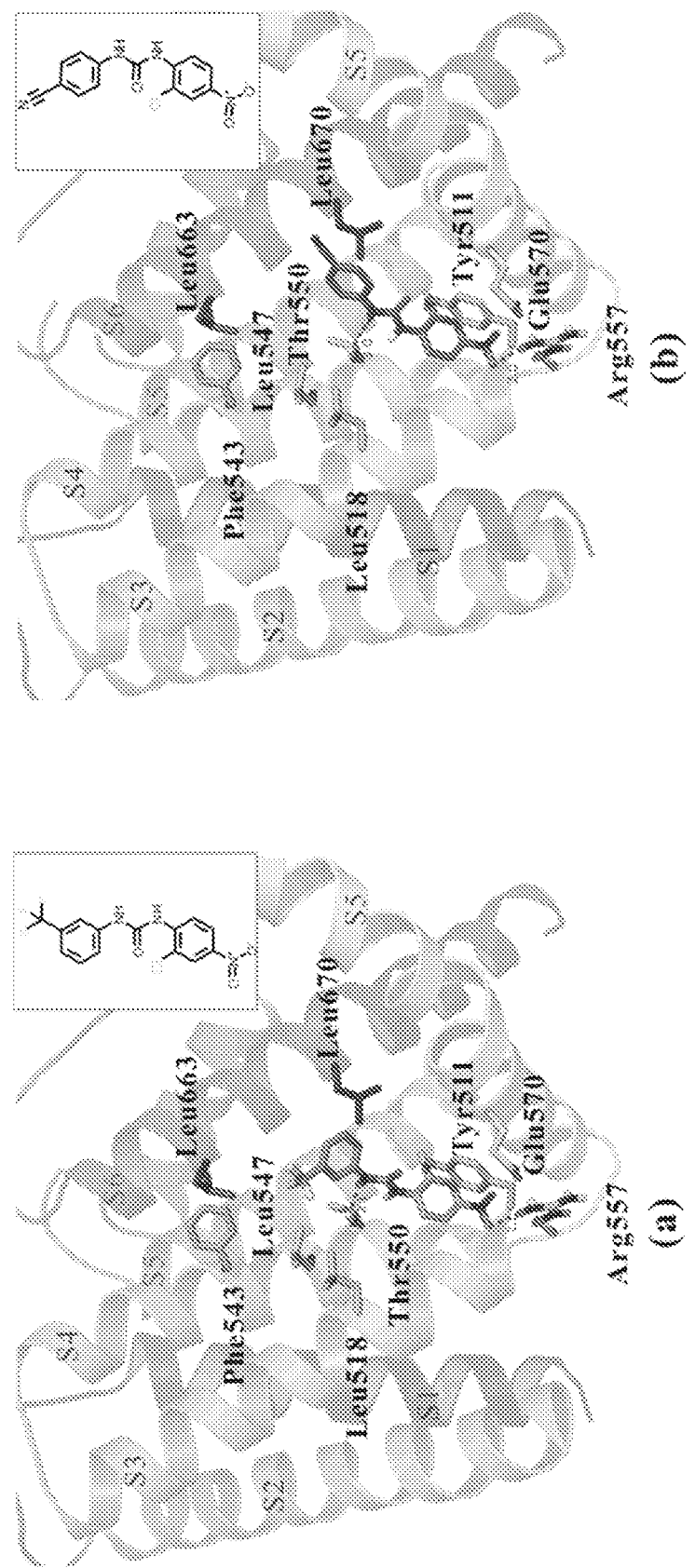
FIGS. 10a and 10b show a comparison of compound 1 with compound 10 indicating that the para-cyano replacement of a meta-trifluoromethyl R2 group affected the activity of the compounds at hTRPV1. (a) The detailed binding pose of compound 1 at TRPV1 (K$_i$: 2.57±0.62 μM). (b) The detailed binding pose of compound 10 at hTRPV1 (35±5% inhibition at 30 μM).
Figure 11:
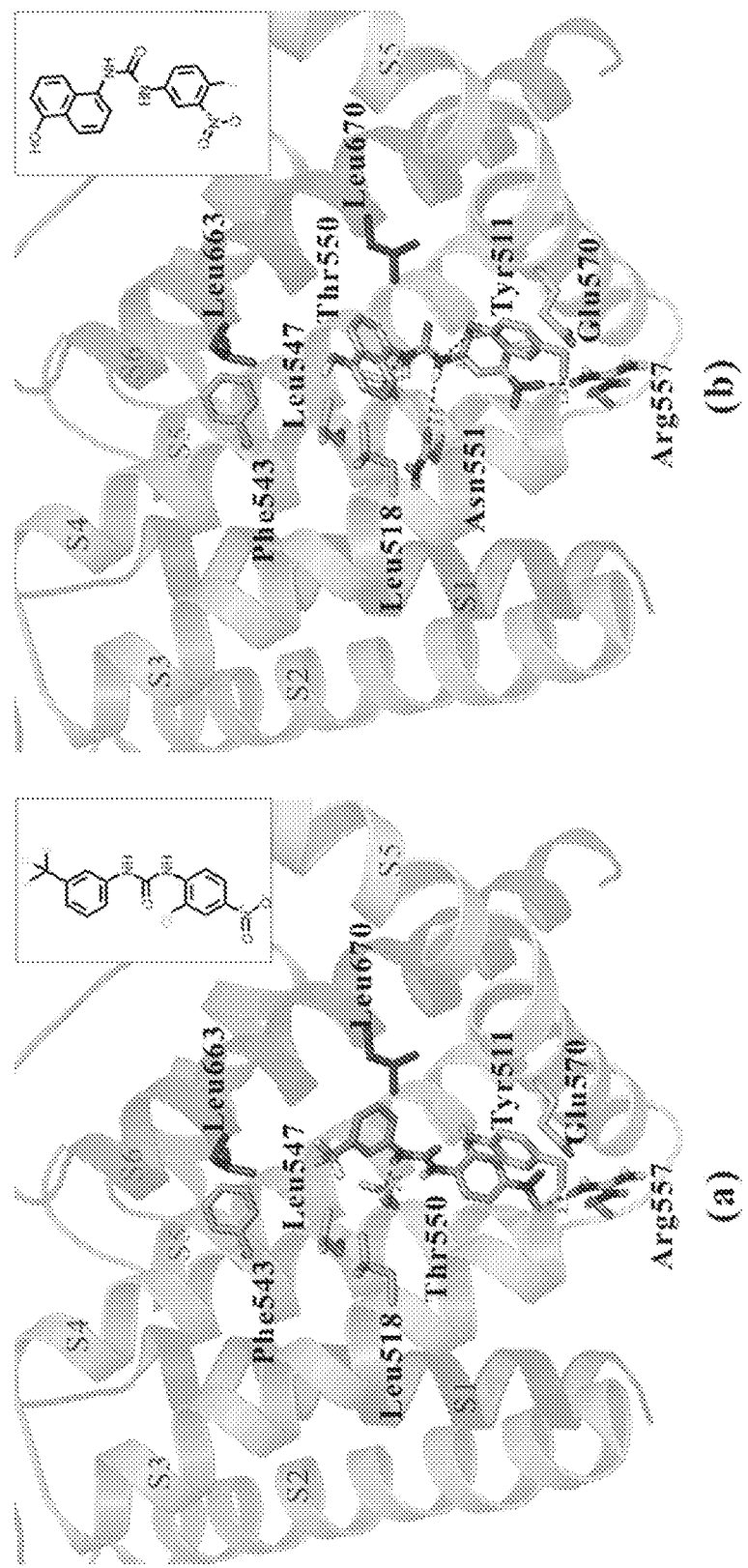
FIGS. 11a and 11b show a comparison of compound 1 with compound 14 indicating that the bulky R2 group replacement enhanced the activity of the ligand at hTRPV1. (a) The detailed binding pose of compound 1 at hTRPV1 (K$_i$: 2.57±±0.62 μM). (b) The detailed binding pose of compound 14 at TRPV1 (K$_i$: 0.47±0.18 μM).
Figure 12:
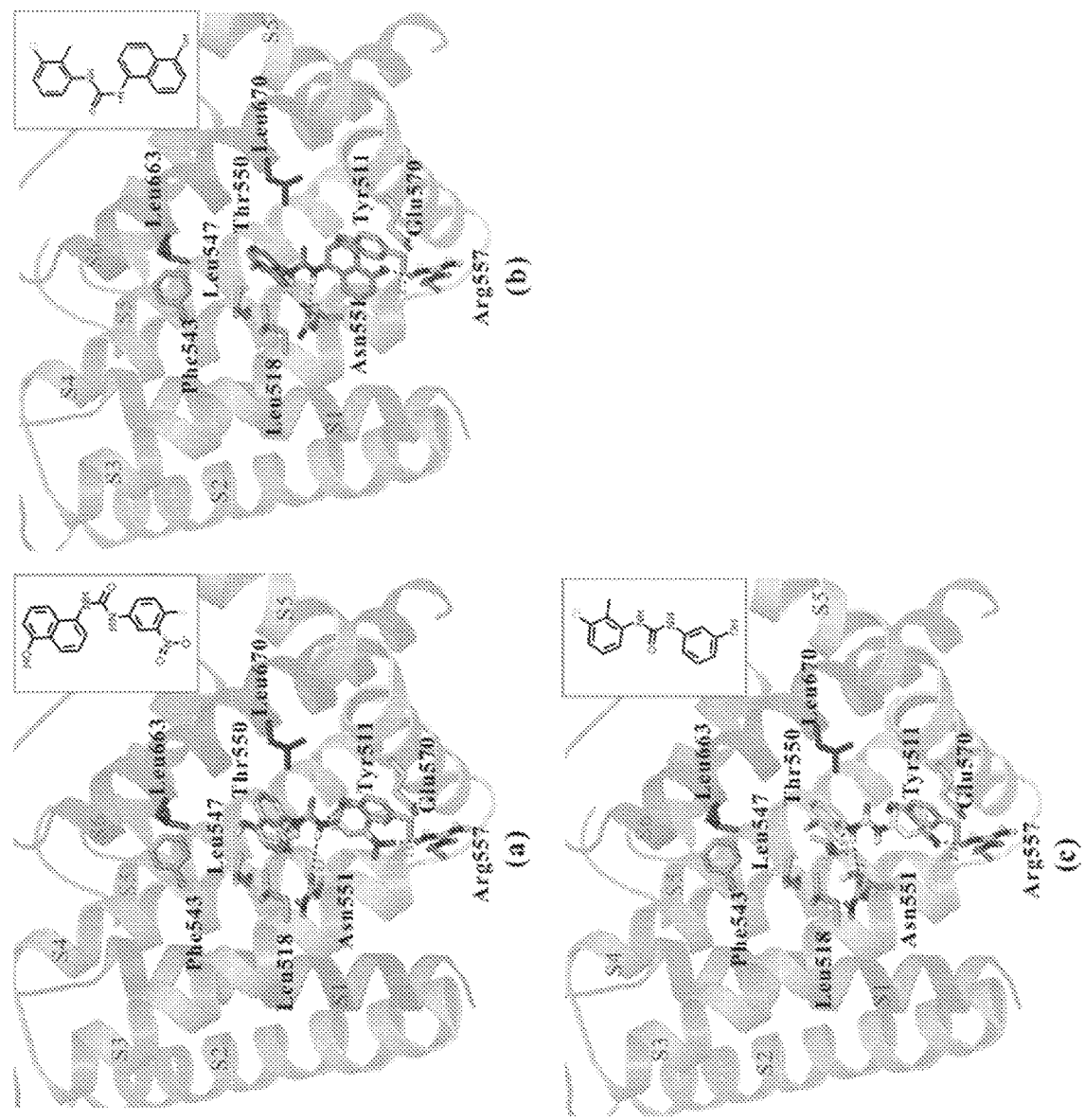
FIGS. 12a and 12b show a comparison of compounds 14-16 indicating that the nitro/hydroxyl group in R1 was important for the activity of inhibitors at hTRPV1. (a) The detailed binding pose of compound 14 at TRPV1 (K$_i$: 0.47±0.18 μM). (b) The detailed binding pose of compound 15 at TRPV1 (K$_i$: 0.49±0.14 μM). (c) The detailed binding pose of compound 16 at TRPV1 (K$_i$: 0.56±0.16 μM).
Figure 13:
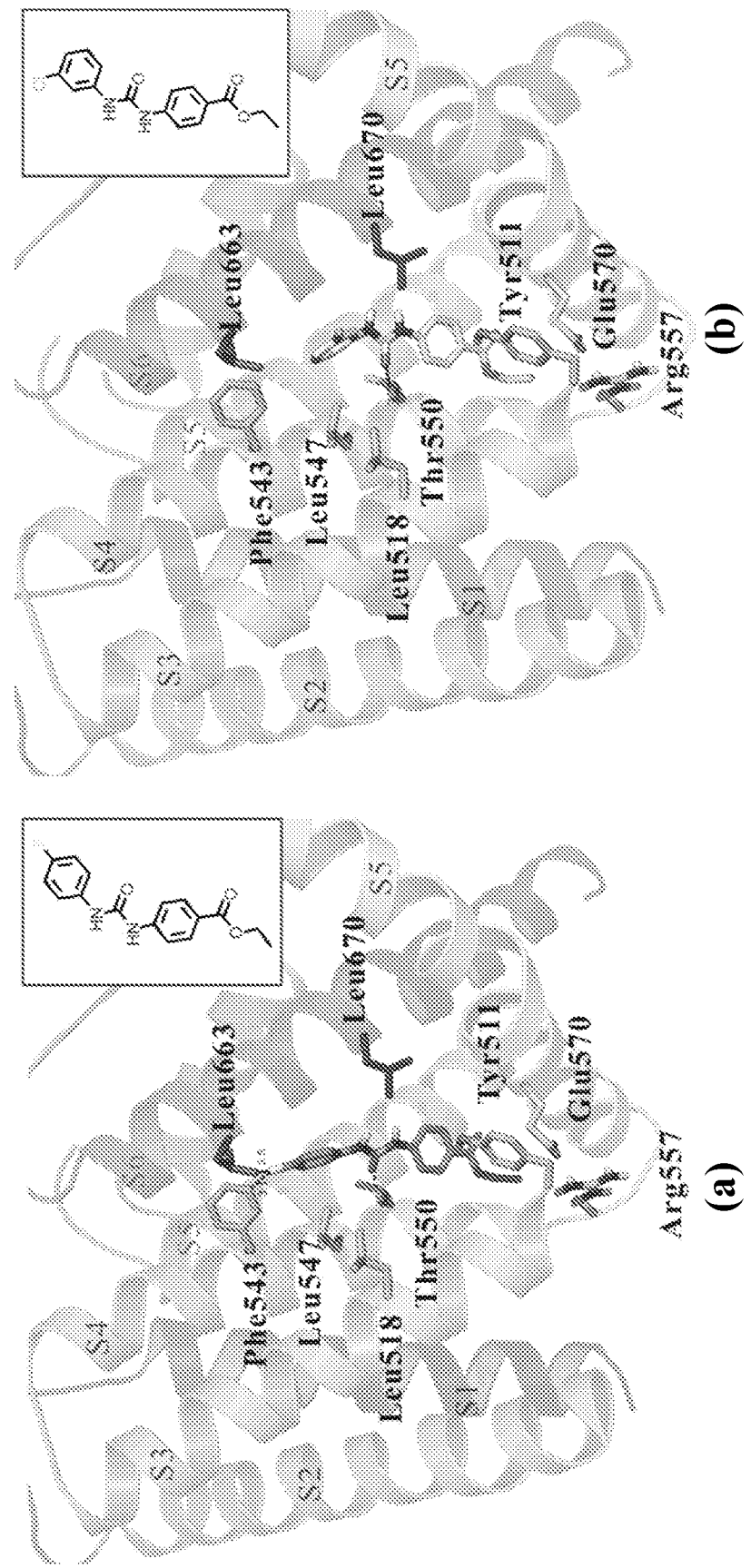
FIGS. 13a and 13b show a comparison of the slight different binding modes of compound 5 (partial agonist) and compound 4 (antagonist) at hTRPV1. (a) The detailed binding pose of compound 5 at hTRPV1 (EC$_{50}$: 2.84±0.21 μM). (b) The detailed binding pose of compound 4 at hTRPV1 (K$_i$: 11.7±1.3 μM).
Figure 14:
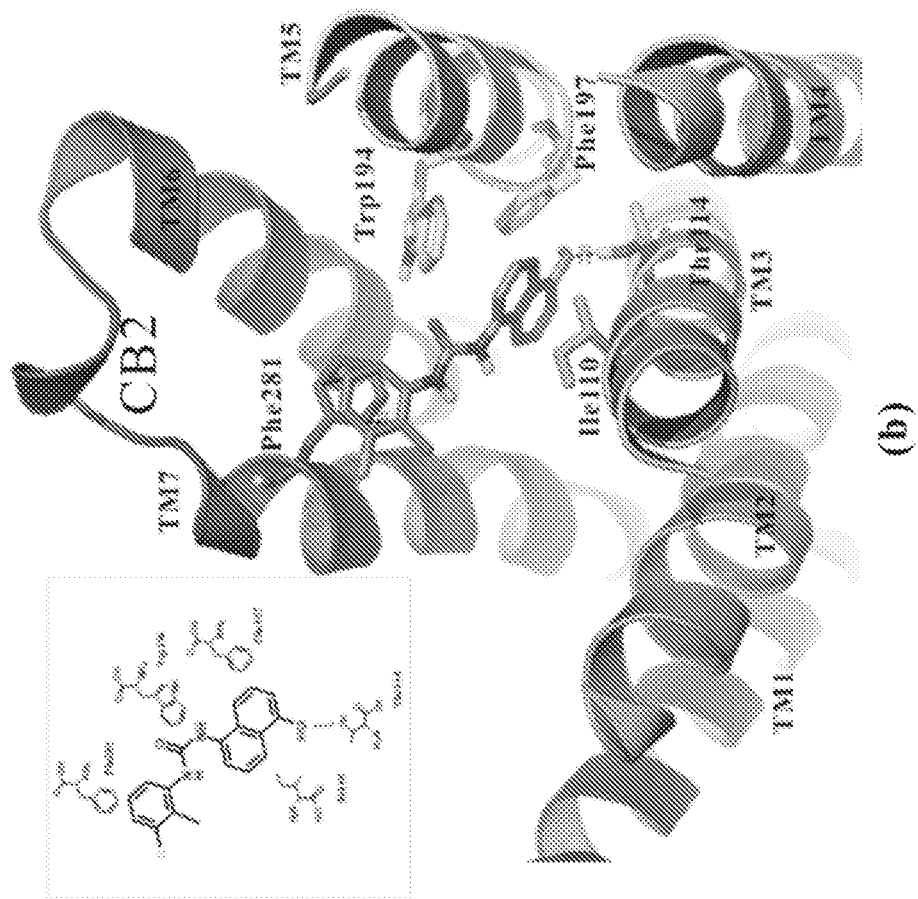
FIGS. 14a and 14b show that compound 15 of TRPV1 had potential binding at CB2. (a) The binding curve (K$_i$: 1.39 μM) of compound 15 at CB2. (b) The detailed binding pose of compound 15 at CB2.
Figure 14:
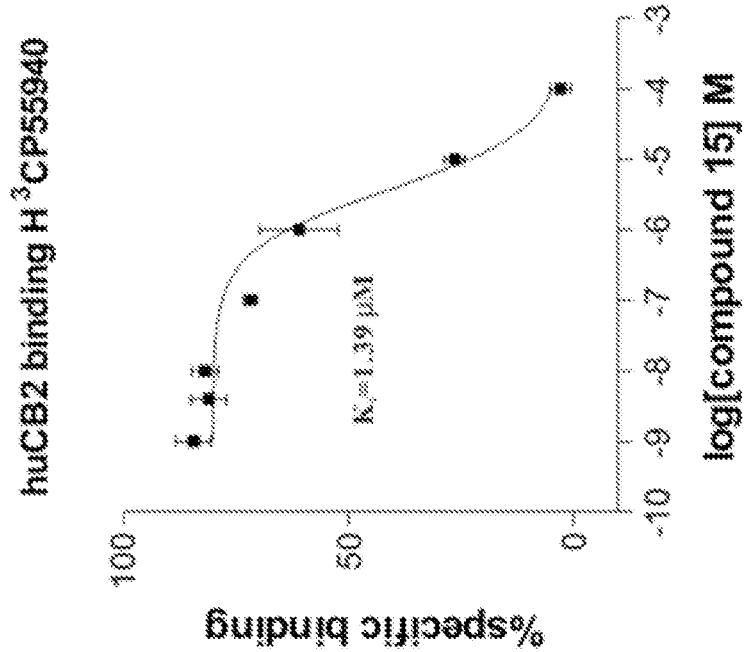
Figure 15:
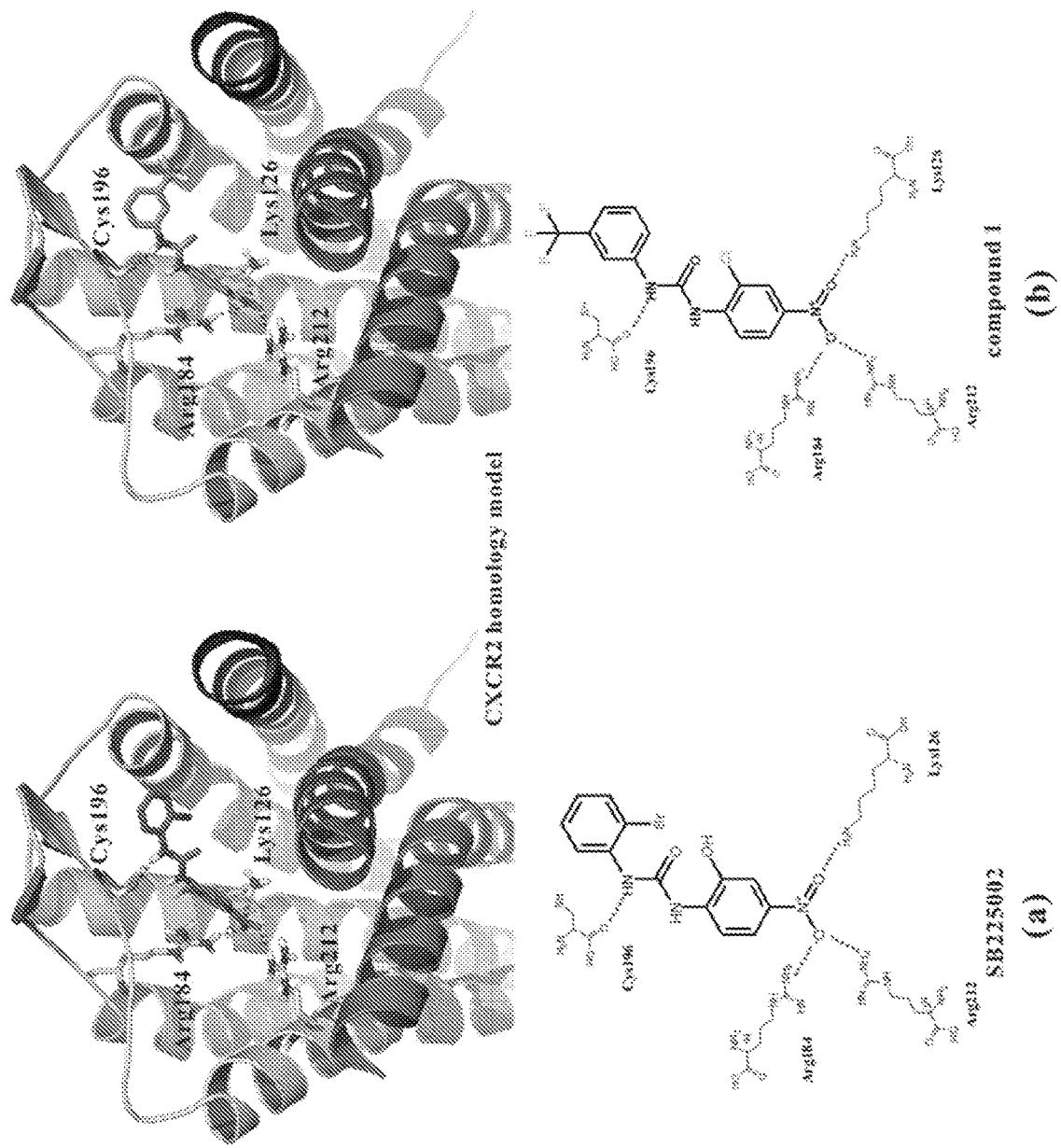
FIG. 15 shows that compound 1 of TRPV1 is predicted to target CXCR2. The potential binding pose of the CXCR2 selective compound SB225002. (b) The potential binding pose of compound 1 at CXCR2. In vitro binding assays are still needed to experimentally validate the predicted binding activity of our compounds with CXCR2.
Figure 16:
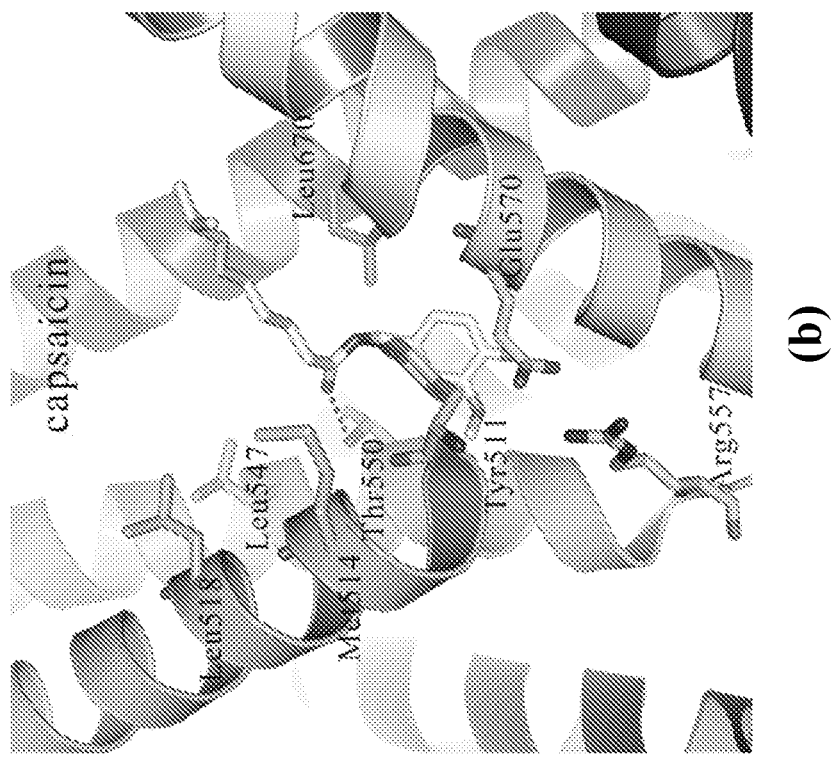
FIGS. 16a and 16b show detailed binding modes of (a) capsaicin and (b) RTX with hTRPV1. Two residues, Tyr511 and Thr550, formed hydrogen bonds with the agonists.
Figure 16:
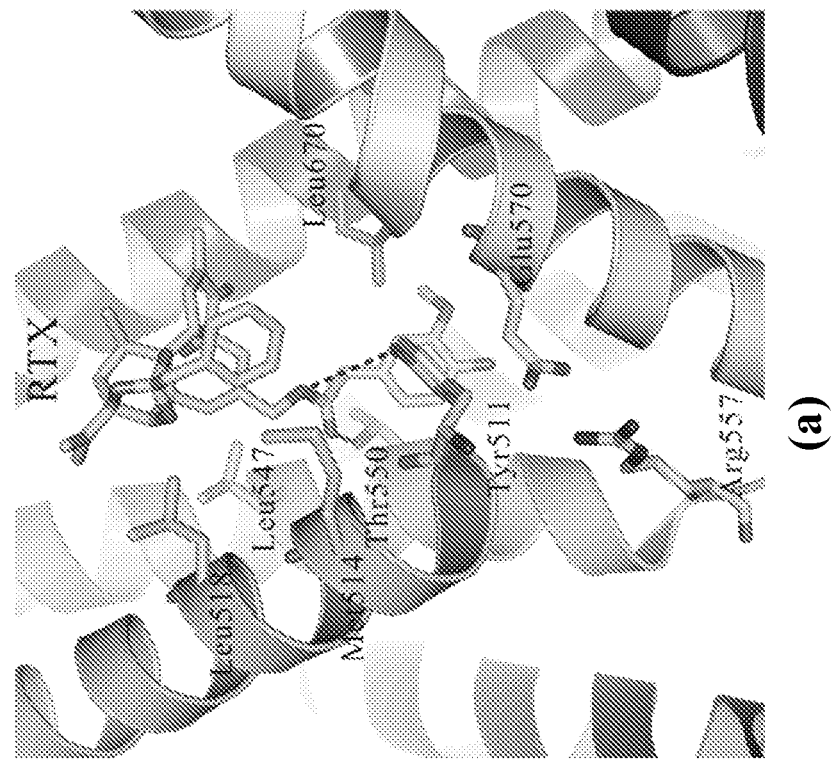
Figure 17:
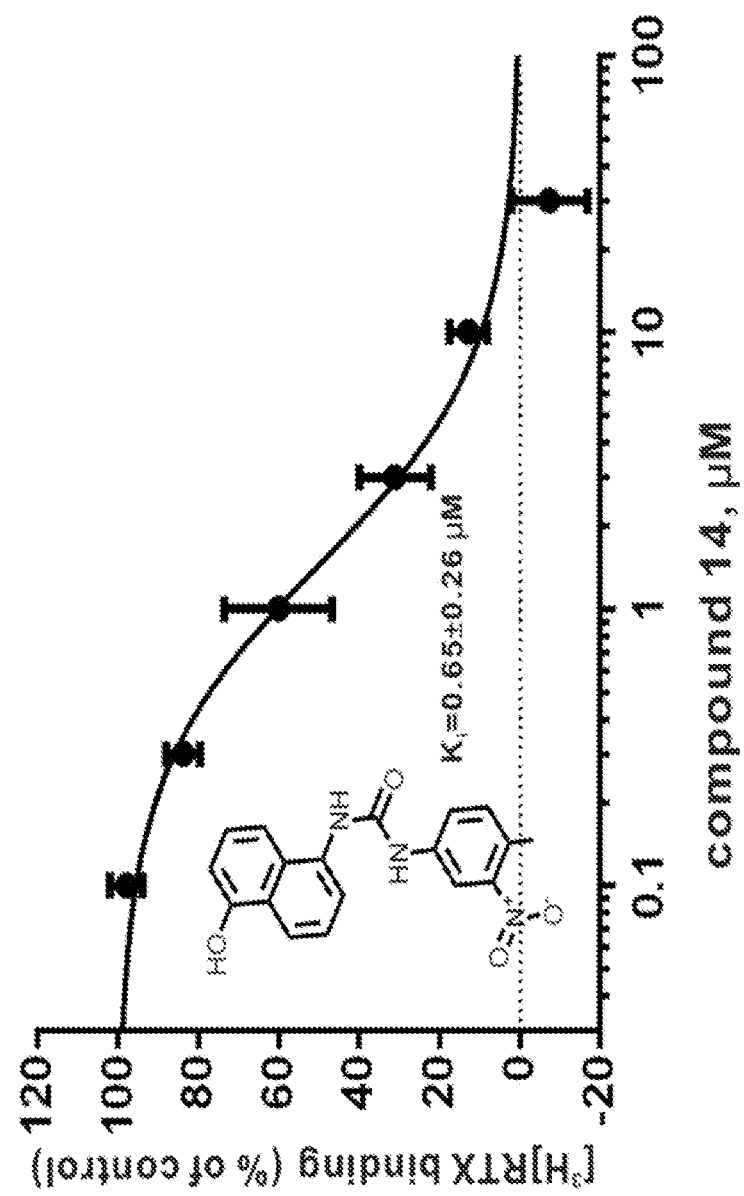
FIG. 17 shows compound 14 inhibited [$^3$H]RTX binding to hTRPV1 with a K$_i$ value of 0.65±0.26 μM.
Figure 18:
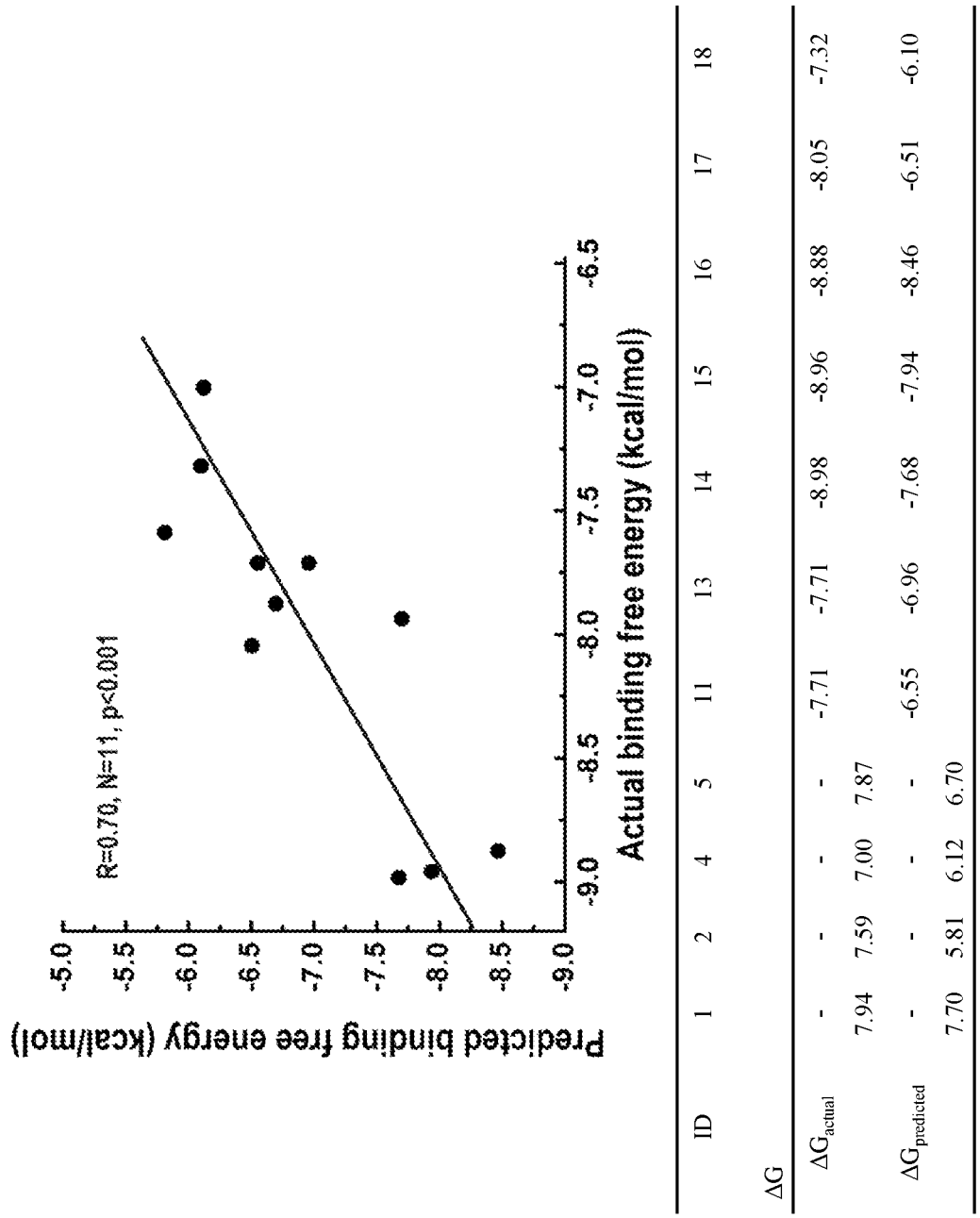
FIG. 18 shows a correlation between the values for the predicted ΔG of the binding based on the modeling and the ΔG derived from the experimental activities ($K_i$) of the 11 compounds in the present work. We converted the experimental activities ($K_i$) to $\Delta G_{actual}$ (x-axis) using the equation $\Delta G_{actual}=RT \ln K_i$ (R: gas constant R, 8.314 J/mol*K; T: absolute temperature, 273.15±37=310.15K, since the T for the binding was measured at 37° C.), comparing with the predicted $\Delta G_{predicted}$ (y-axis).
Figure 19:
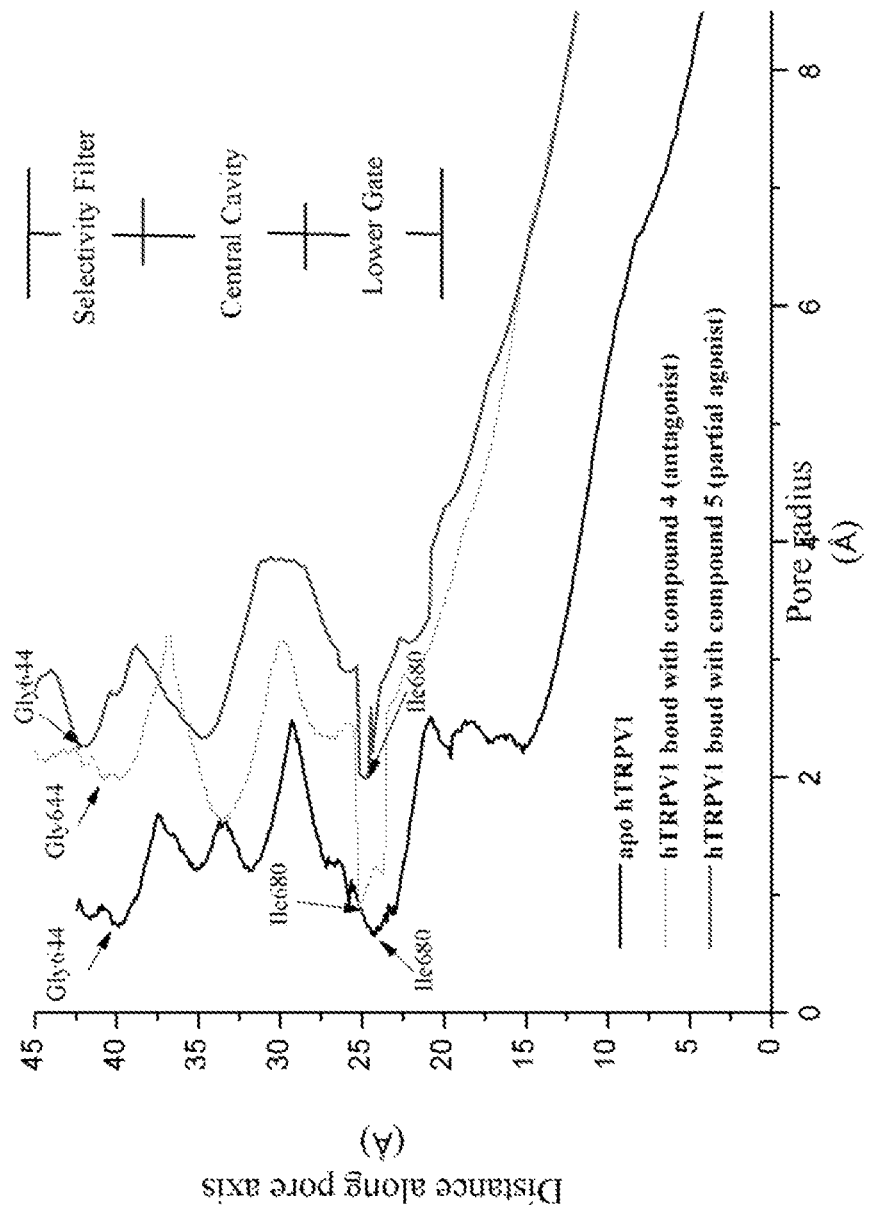
FIG. 19 shows the comparisons of pore radius and conformational changes of hTRPV1 bound with compound 4 and bound with compound 5. The pore radius along the channel for apo hTRPV1, hTRPV1-compound 4 (average conformation during the last 2 ns), and hTRPV1-compound 5 (average conformation during the last 2 ns).
Figure 20:
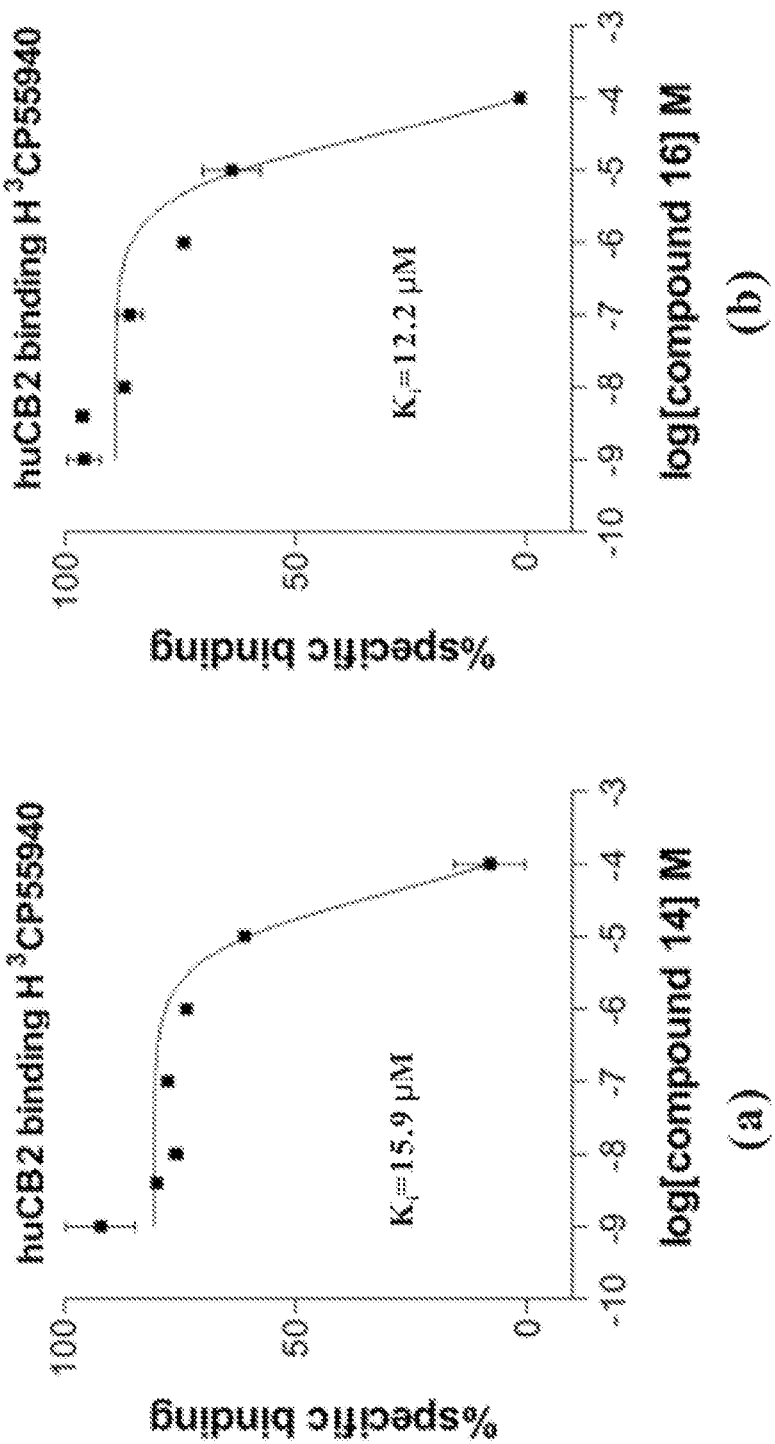
FIGS. 20a and 20b show compounds (a) 14 and (b) 16 had weak binding activity with $K_i$ values of 15.9 and 12.2 μM at CB2.

Compounds of the present disclosure include novel compounds represented by Formula (I):

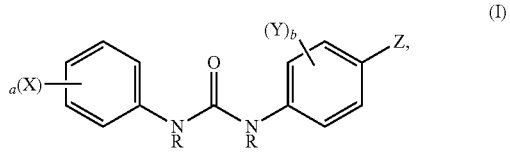

wherein:

X is independently in each instance halogen, OH, amino, COOH, $CONH_2$, $SO_3H$, $PO_3H_2$, CN, SH, $N(R')_2$, $NO_2$, $CF_3C_1-C_6$ perfluoroalkyl, NHC(O)—$C_1-C_6$ alkyl, NHC(O)—$C_1-C_6$ perfluoroalkyl, ($C_1-C_6$)alkyl, ($C_1-C_6$)alkoxy, ($C_1-C_6$)haloalkoxy, ($C_1-C_6$)haloalkyl, ($C_2-C_6$)alkenyl, ($C_2-C_6$)alkynyl, —$NH_2$, —NH($C_1-C_6$)alkyl, —N[($C_1-C_6$)alkyl]$_2$, —CN, ($C_3-C_8$)heteroaryl, ($C_3-C_8$)heterocycloalkyl, ($C_3-C_8$)cycloalkyl, ($C_3-C_8$)aryl, ($C_3-C_8$)heterocycloalkyl-($C_1-C_6$)alkylene-, ($C_3-C_8$)heteroaryl-($C_1-C_6$)alkylene-, ($C_3-C_8$)aryl($C_1-C_6$)alkylene-, ($C_3-C_8$)aryl($C_1-C_6$)alkenylene-, or ($C_1-C_6$)alkyl-($C_3-C_8$)arylene; Y is independently in each instance halogen, OH, amino, COOH, $CONH_2$, $SO_3H$, $PO_3H_2$, CN, SH, $N(R')_2$, $NO_2$, $CF_3C_1-C_6$ perfluoroalkyl, NHC(O)—$C_1-C_6$ alkyl, NHC(O)—$C_1-C_6$ perfluoroalkyl, ($C_1-C_6$)alkyl, ($C_1-C_6$)alkoxy, ($C_1-C_6$)haloalkoxy, ($C_1-C_6$)haloalkyl, ($C_2-C_6$)alkenyl, ($C_2-C_6$)alkynyl, —$NH_2$, —NH($C_1-C_6$)alkyl, —N[($C_1-C_6$)alkyl]$_2$, —CN, ($C_3-C_8$)heteroaryl, ($C_3-C_8$)heterocycloalkyl, ($C_3-C_8$)cycloalkyl, ($C_3-C_8$)aryl, ($C_3-C_8$)heterocycloalkyl-($C_1-C_6$)alkylene-, ($C_3-C_8$)heteroaryl-($C_1-C_6$)alkylene-, ($C_3-C_8$)aryl($C_1-C_6$)alkylene-, ($C_3-C_8$)aryl($C_1-C_6$)alkenylene-, or ($C_1-C_6$)alkyl-($C_3-C_8$)arylene;

Z is halogen, OH, amino, COOH, $CONH_2$, $SO_3H$, $PO_3H_2$, CN, SH, $N(R')_2$, $NO_2$, $CF_3C_1-C_6$ perfluoroalkyl, NHC(O)—$C_1-C_6$ alkyl, NHC(O)—$C_1-C_6$ perfluoroalkyl, ($C_1-C_6$)alkyl, ($C_1-C_6$)alkoxy, ($C_1-C_6$)haloalkoxy, ($C_1-C_6$)haloalkyl, ($C_2-C_6$)alkenyl, ($C_2-C_6$)alkynyl, —$NH_2$, —NH($C_1-C_6$)alkyl, —N[($C_1-C_6$)alkyl]$_2$, —CN, ($C_3-C_8$)heteroaryl, ($C_3-C_8$)heterocycloalkyl, ($C_3-C_8$)cycloalkyl, ($C_3-C_8$)aryl, ($C_3-C_8$)heterocycloalkyl-($C_1-C_6$)alkylene-, ($C_3-C_8$)heteroaryl-($C_1-C_6$)alkylene-, ($C_3-C_8$)aryl($C_1-C_6$)alkylene-, ($C_3-C_8$)aryl($C_1-C_6$)alkenylene-, or ($C_1-C_6$)alkyl-($C_3-C_8$)arylene;

R is independently in each instance H, —OH, ($C_1-C_6$) alkyl, ($C_1-C_6$) perfluoroalkyl; ($C_1-C_6$)alkoxy, ($C_1-C_6$)haloalkoxy, ($C_1-C_6$)haloalkyl, ($C_2-C_6$)alkenyl, ($C_2-C_6$)alkynyl, —$NH_2$, —NH($C_1-C_6$)alkyl, —N[($C_1-C_6$)alkyl]$_2$, —CN, ($C_3-C_8$)heteroaryl, ($C_3-C_8$)heterocycloalkyl, ($C_3-C_8$)cycloalkyl, ($C_3-C_8$)aryl, ($C_3-C_8$)heterocycloalkyl-($C_1-C_6$)alkylene-, ($C_3-C_8$)heteroaryl-($C_1-C_6$)alkylene-, ($C_3-C_8$)aryl($C_1-C_6$)alkylene-, ($C_3-C_8$)aryl($C_1-C_6$)alkenylene-, or ($C_1-C_6$)alkyl-($C_3-C_8$)arylene;

R' is independently in each instance H, —OH, ($C_1-C_6$) alkyl, ($C_1-C_6$) perfluoroalkyl; ($C_1-C_6$)alkoxy, ($C_1-C_6$)haloalkoxy, ($C_1-C_6$)haloalkyl, ($C_2-C_6$)alkenyl, ($C_2-C_6$)alkynyl, —$NH_2$, —NH($C_1-C_6$)alkyl, —N[($C_1-C_6$)alkyl]$_2$, —CN, ($C_3-C_8$)heteroaryl, ($C_3-C_8$)heterocycloalkyl, ($C_3-C_8$)cycloalkyl, ($C_3-C_8$)aryl, ($C_3-C_8$)heterocycloalkyl-($C_1-C_6$)alkylene-, ($C_3-C_8$)heteroaryl-($C_1-C_6$)alkylene-, ($C_3-C_8$)aryl($C_1-C_6$)alkylene-, ($C_3-C_8$)aryl($C_1-C_6$)alkenylene-, or ($C_1-C_6$)alkyl-($C_3-C_8$)arylene;

a is an integer of 0 to 5; and b is an integer of 0 to 4, wherein the alkyl moieties are optionally substituted by one or more halogen, or a pharmaceutically acceptable salt or solvate thereof.

In some embodiments, in Formula (I),

X is independently in each instance halogen, $C_1-C_6$ alkyl, $C_1-C_6$ perfluoroalkyl, NHC(O)—$C_1-C_6$ alkyl, NHC(O)—$C_1-C_6$ perfluoroalkyl, $N(R')_2$, $C_1-C_6$ alkyloxy, pyrrolidine;

Y is independently in each instance halogen, $C_1-C_6$ alkyl, $C_1-C_6$ perfluoroalkyl, NHC(O)—$C_1-C_6$ alkyl, NHC(O)—$C_1-C_6$ perfluoroalkyl, $N(R')_2$, $C_1-C_6$ alkyloxy, pyrrolidine;

Z is $N(R')_2$, $NO_2$ or

R is independently in each instance H, $C_1-C_6$ alkyl;

R' is independently in each instance H, $C_1-C_6$ alkyl, $C_1-C_6$ perfluoroalkyl;

a is an integer of 1 to 5; and b is an integer of 0 to 4, wherein the alkyl moieties are optionally substituted by one or more halogen, or any pharmaceutically acceptable salt or solvate thereof.

In some embodiments, the halogen is fluoro.

In some embodiments, Z is $N(R')_2$ or $NO_2$ or

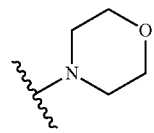

in the para or meta position. In some embodiments, Z is a para F or Cl moiety.

In some embodiments, a is an integer of 1 to 5; and b is an integer of 0 to 4.

In some embodiments, X is

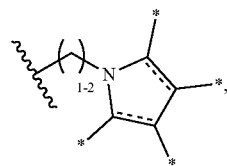

where ⌒ represents an optional bond; * is independently H, D, Cl, F, Me, Et, OMe, or CF$_3$, for example,

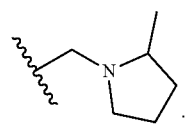 [SMILES: *CN1CCCC1C]

In some embodiments, X is

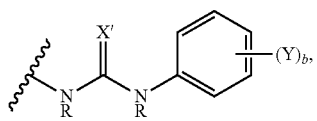

where X' is O or S, and R, Y and b are defined above, for example,

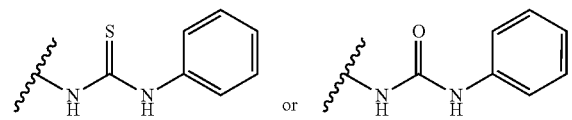

In some embodiments, X is selected from the group consisting of D, Cl, F, (CH$_2$)$_{0-5}$CH$_3$, (e.g., Me, Et), OMe, CF$_3$, CN, C(O)NR$_2$, COO(CH$_2$)$_{0-5}$CH$_3$, COO(CH$_2$)$_{0-5}$CF$_3$, (CH$_2$)$_{1-5}$OH, (CH$_2$)$_{0-5}$—O—(CH$_2$)$_{1-5}$, (CH$_2$)$_{0-5}$—S—(CH$_2$)$_{1-5}$, and (CH$_2$)$_{0-5}$—NR—(CH$_2$)$_{1-5}$.

In some embodiments, Y is

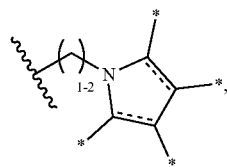

where ⌒ represents an optional bond; * is independently H, D, Cl, F, Me, Et, OMe, or CF$_3$, for example,

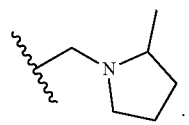 [SMILES: *CN1CCCC1C]

In some embodiments, Y is

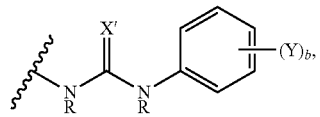

where X' is O or S, and R, Y and b are defined above, for example,

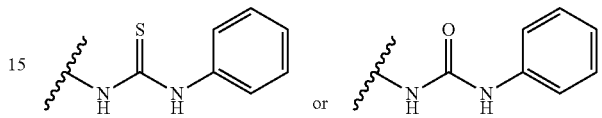

In some embodiments, Y is selected from the group consisting of D, Cl, F, (CH$_2$)$_{0-5}$CH$_3$, (e.g., Me, Et), OMe, CF$_3$, CN, C(O)NR$_2$, COO(CH$_2$)$_{0-5}$CH$_3$, COO(CH$_2$)$_{0-5}$CF$_3$, (CH$_2$)$_{1-5}$OH, (CH$_2$)$_{0-5}$—O—(CH$_2$)$_{1-5}$, (CH$_2$)$_{0-5}$—S—(CH$_2$)$_{1-5}$, and (CH$_2$)$_{0-5}$—NR—(CH$_2$)$_{1-5}$.

In some embodiments, the compounds of the present disclosure include novel compounds represented by Formula (Ia):

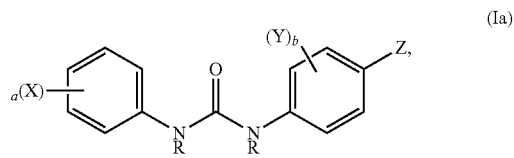

or any pharmaceutically acceptable salt or solvate thereof.

In further embodiments, the compounds of the present disclosure include novel compounds represented by Formula (Ia') or (Ia'') or (Ia''') or (Ia'''') or (Ia''''') or one of (Ia$^{6-10}$):

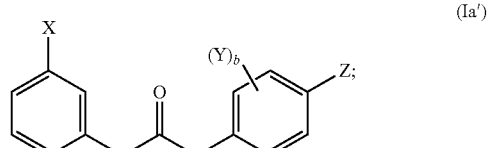

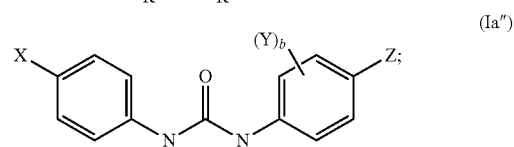

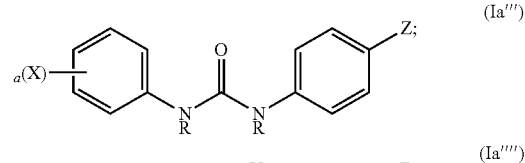

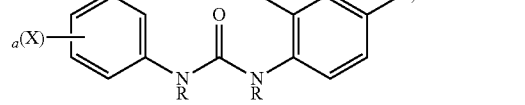

-continued

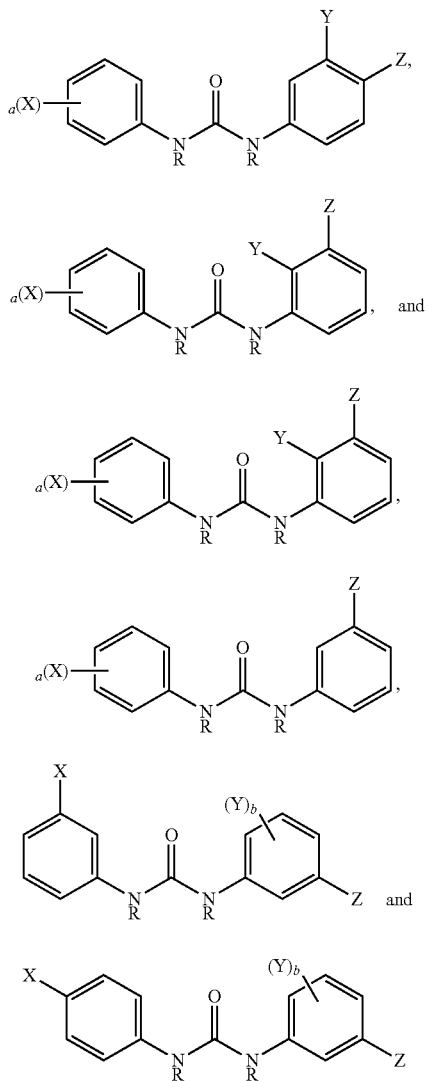

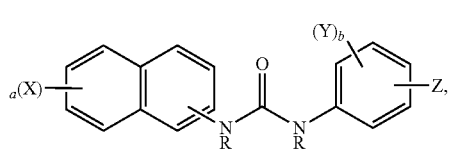

or any pharmaceutically acceptable salt or solvate thereof. The variables of formulae (a), (Ia'), (Ia''), (Ia'''), (Ia''''), (Ia'''''), and (Ia$^{6-10}$) are the same as for Formula (I).

In some embodiments, when X in formula (Ia') is F, then Y is not methyl, and when X is Cl, then Y is not Cl, and in Formula (Ia''') when X is methyl and a is two, R is not in each instance H.

Other embodiments include compounds represented by Formula (Ib):

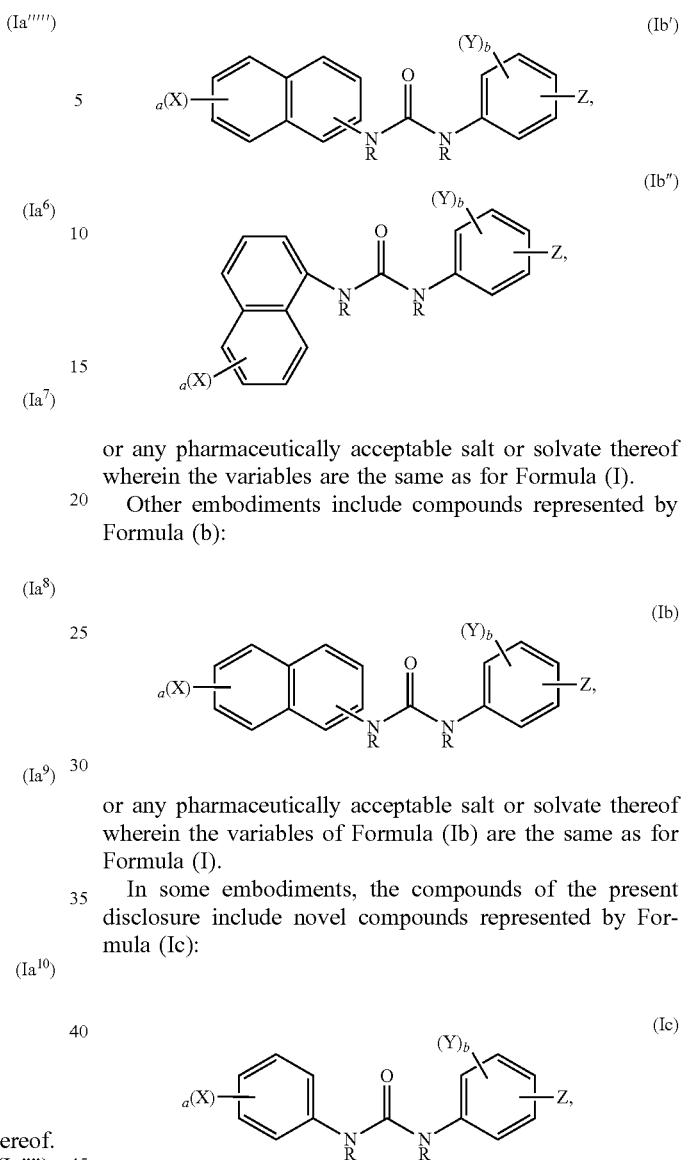

or any pharmaceutically acceptable salt or solvate thereof wherein the variables of Formula (b) are the same as for Formula (I).

Some embodiments include compounds represented by Formula (Ib') and (Ib")

or any pharmaceutically acceptable salt or solvate thereof wherein the variables are the same as for Formula (I).

Other embodiments include compounds represented by Formula (b):

or any pharmaceutically acceptable salt or solvate thereof wherein the variables of Formula (Ib) are the same as for Formula (I).

In some embodiments, the compounds of the present disclosure include novel compounds represented by Formula (Ic):

or any pharmaceutically acceptable salt or solvate thereof, wherein two of X and/or two of Y are present on adjacent atoms, and together form a five or six-membered aryl, heteroaryl, heterocyclic or cyclic ring that is optionally substituted by one or more halogen, OH, amino, COOH, CONH$_2$, SO$_3$H, PO$_3$H$_2$, CN, SH, N(R')$_2$, NO$_2$, CF$_3$C$_1$-C$_6$ perfluoroalkyl, NHC(O)—C$_1$-C$_6$ alkyl, NHC(O)—C$_1$-C$_6$ perfluoroalkyl, (C$_1$-C$_6$)alkyl, (C$_1$-C$_6$)alkoxy, (C$_1$-C$_6$)haloalkoxy, (C$_1$-C$_6$)haloalkyl, (C$_2$-C$_6$)alkenyl, (C$_2$-C$_6$)alkynyl, —NH$_2$, —NH(C$_1$-C$_6$)alkyl, —N[(C$_1$-C$_6$)alkyl]$_2$, —CN, (C$_3$-C$_8$)heteroaryl, (C$_3$-C$_8$)heterocycloalkyl, (C$_3$-C$_8$)cycloalkyl, (C$_3$-C$_8$)aryl, (C$_3$-C$_8$)heterocycloalkyl-(C$_1$-C$_6$)alkylene-, (C$_3$-C$_8$)heteroaryl-(C$_1$-C$_6$)alkylene-, (C$_3$-C$_8$)aryl (C$_1$-C$_6$)alkylene-, (C$_3$-C$_8$)aryl(C$_1$-C$_6$)alkenylene-, or (C$_1$-C$_6$)alkyl-(C$_3$-C$_8$)arylene, and the remaining variables of Formula (Ic) are the same as for Formula (I).

In some embodiments, the two of X and/or two of Y are present on adjacent atoms, and together form a five or six-membered aryl ring. In some embodiments, the two of X and/or two of Y are present on adjacent atoms, and together form a five or six-membered heteroaryl ring. In some embodiments, the two of X and/or two of Y are present on adjacent atoms, and together form a five or six-membered heterocyclic ring. In some embodiments, the two of X and/or two of Y are present on adjacent atoms, and together form a five or six-membered cyclic ring. In some embodiments, the heteroatom is N. In some embodiments, the heteroatom is O. In some embodiments, the heterocycle/heteroaryl is selected from pyrrole, 1-pyrroline, 2-pyrroline, 3-pyrroline, pyrrolidone, imidazole, imidazoline, imidazolidine, pyrazole, 2-pyrazoline, 3-pyrazoline, pyrazolidine, 1,3,4-triazole, 1,2,3-triazole, 1,2,4-triazole, tetrazole, pentazole, pyridine, pyridazine, pyrimidine, pyrazine, triazine, 1,4-dihydropyridine, dihydropyrazine, piperidine, and piperazine.

In some embodiments, the two X are present on adjacent atoms, and together form a five or six-membered aryl or heteroaryl or heterocyclic or cyclic ring. In some embodiments, the two Y are present on adjacent atoms, and together form a five or six-membered aryl or heteroaryl or heterocyclic or cyclic ring. In some embodiments, the two X and the two Y are present on adjacent atoms, and each set together, independently, form a five or six-membered aryl or heteroaryl or heterocyclic or cyclic ring.

Compounds of Formula (Ic) include:

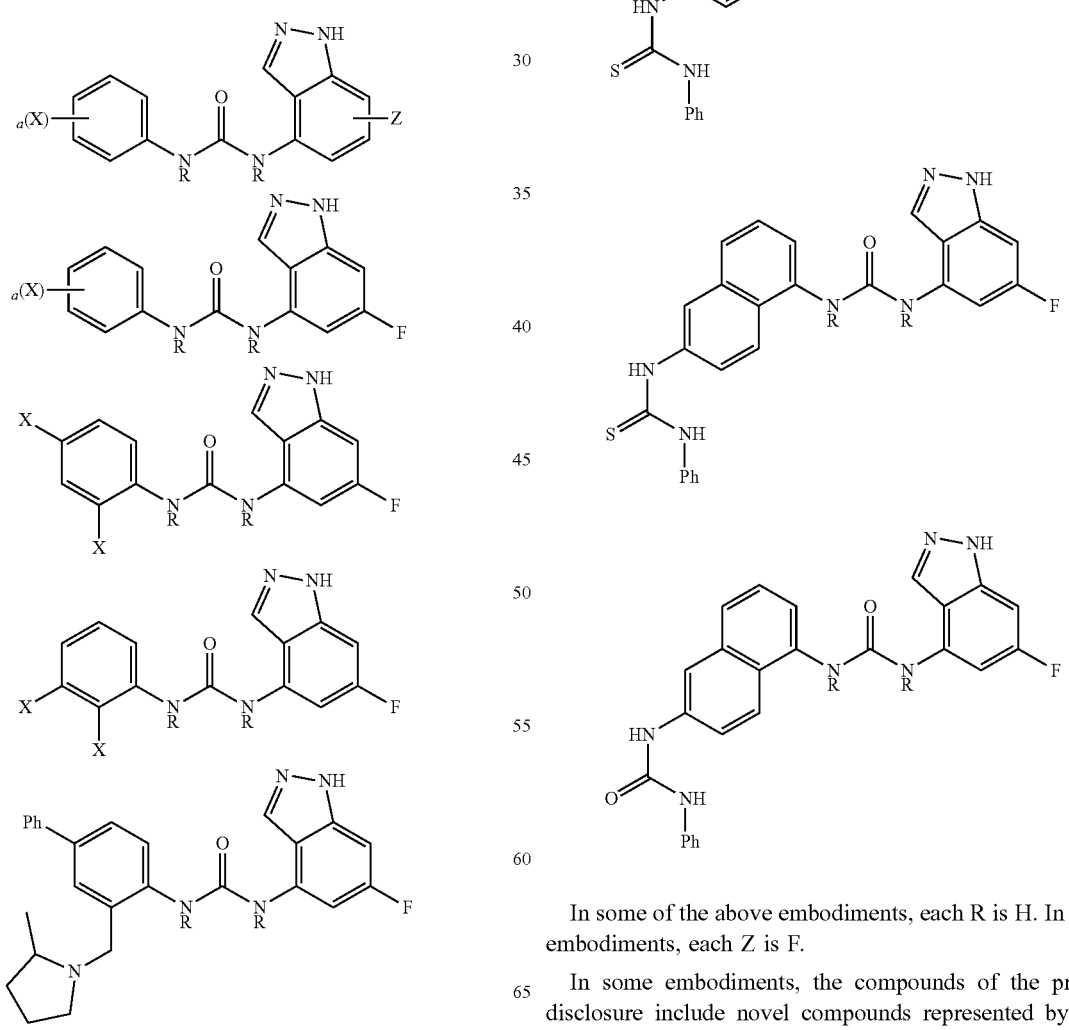

In some of the above embodiments, each R is H. In some embodiments, each Z is F.

In some embodiments, the compounds of the present disclosure include novel compounds represented by Formula (Id):

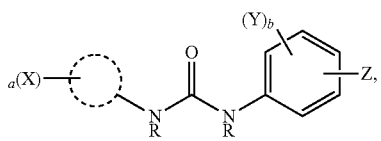

(Id)

or any pharmaceutically acceptable salt or solvate thereof, wherein

is a 6- or 10-membered aryl (e.g., phenyl or napthyl), and the variables of Formula (Id) are the same as for Formula (I) or (Ic).

In some embodiments, the compounds of the present disclosure include novel compounds represented by Formula (Ie):

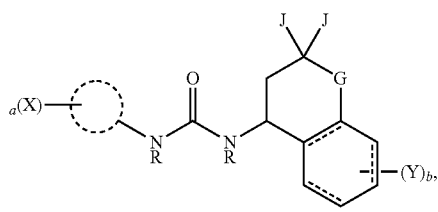

(Ie)

or any pharmaceutically acceptable salt or solvate thereof, wherein

is a 6- or 10-membered aryl (e.g., phenyl or napthyl);

$\cdots$ represents an optional bond;

J is independently a $C_1$-$C_6$ alkyl substituted by one or more halogen, OH, amino, COOH, CONH$_2$, SO$_3$H, PO$_3$H$_2$, CN, SH, N(R')$_2$, NO$_2$, CF$_3$ $C_1$-$C_6$ perfluoroalkyl, NHC(O)—$C_1$-$C_6$ alkyl, NHC(O)—$C_1$-$C_6$ perfluoroalkyl, ($C_1$-$C_6$)alkyl, ($C_1$-$C_6$)alkoxy, ($C_1$-$C_6$)haloalkoxy, ($C_1$-$C_6$)haloalkyl, ($C_2$-$C_6$)alkenyl, ($C_2$-$C_6$)alkynyl, —NH$_2$, —NH($C_1$-$C_6$)alkyl, —N[($C_1$-$C_6$)alkyl]$_2$, —CN, ($C_3$-$C_8$)heteroaryl, ($C_3$-$C_8$)heterocycloalkyl, ($C_3$-$C_8$)cycloalkyl, ($C_3$-$C_8$)aryl, ($C_3$-$C_8$)heterocycloalkyl-($C_1$-$C_6$)alkylene-, ($C_3$-$C_8$)heteroaryl-($C_1$-$C_6$)alkylene-, ($C_3$-$C_8$)aryl($C_1$-$C_6$)alkylene-, ($C_3$-$C_8$)aryl($C_1$-$C_6$)alkenylene-, or ($C_1$-$C_6$)alkyl-($C_3$-$C_8$)arylene; G is CR$_2$, O, or NR;

and the variables of Formula (Ie) are the same as for Formula (I).

In some embodiments, J is selected from $C_1$-$C_6$-alkyl-halogen (e.g., Cl or F), $C_1$-$C_6$-alkyl-hydroxyl, and $C_1$-$C_6$ perfluoroalkyl.

In some embodiments, G is O. In some embodiments, each of $\cdots$ is present.

Additional embodiments of Formulae (Ie) include:

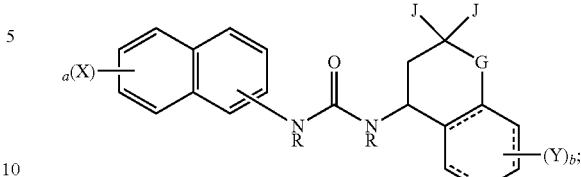

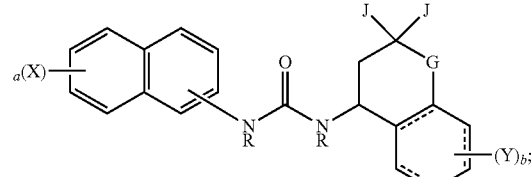

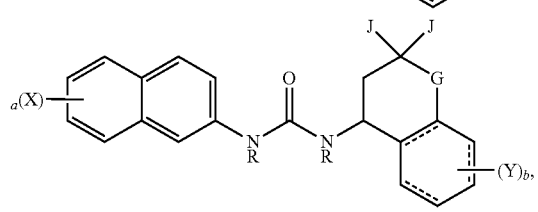

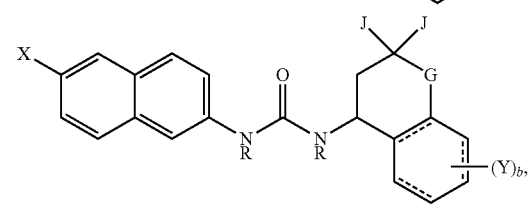

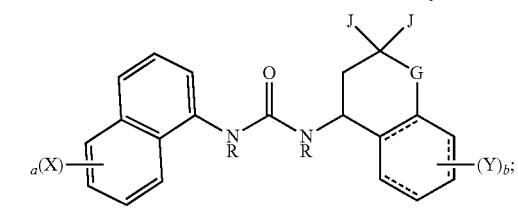

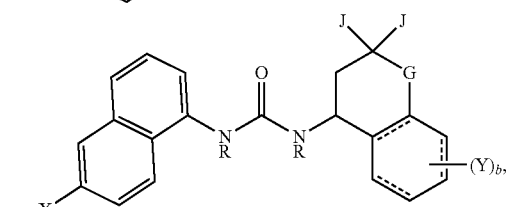

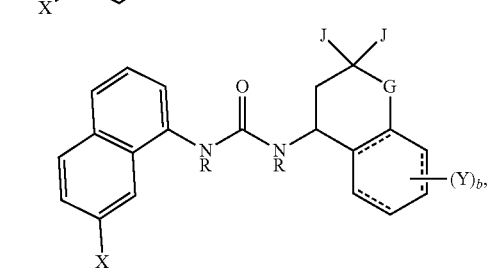

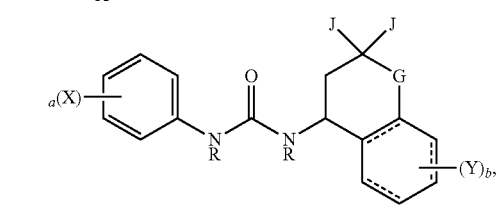

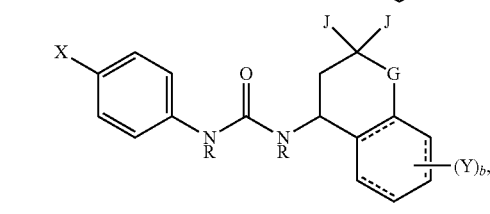

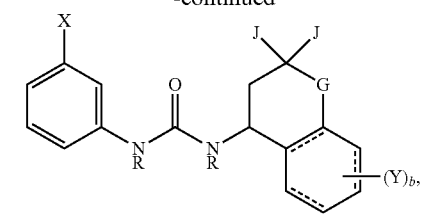
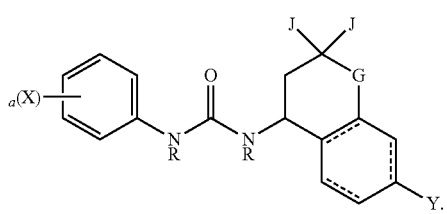
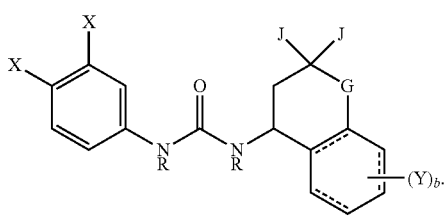
Compounds of Formulae (Ie) include:
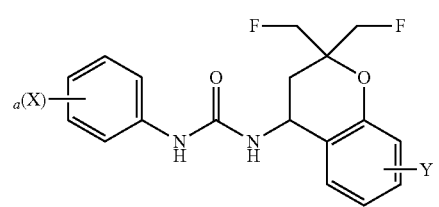
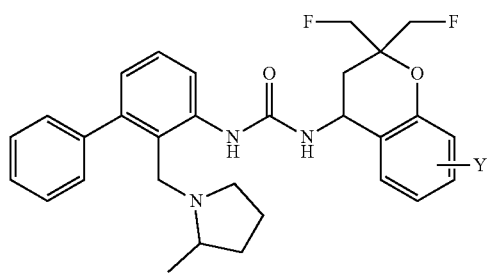
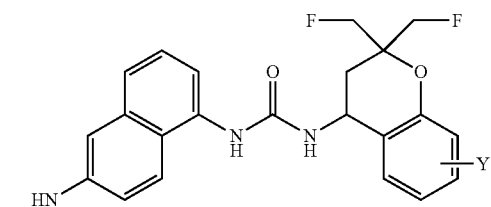
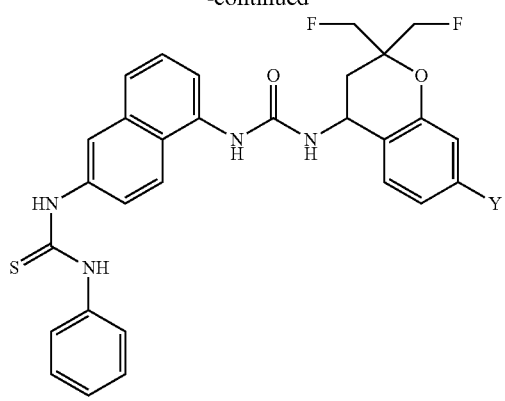
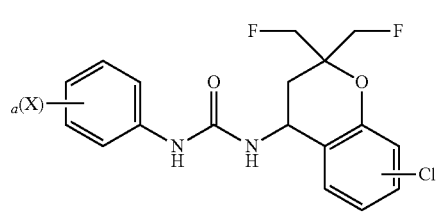
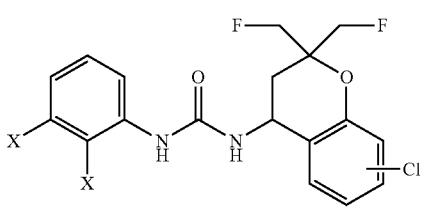
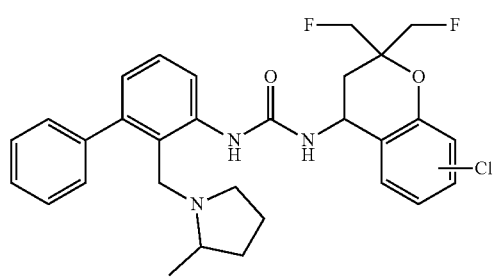
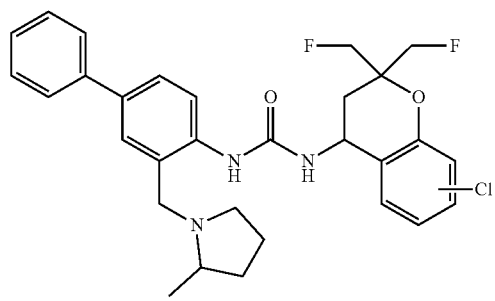
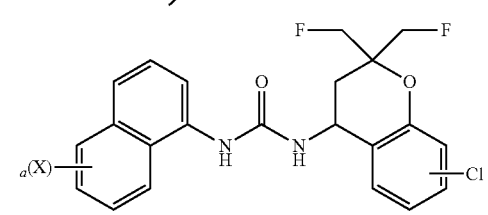

17

-continued

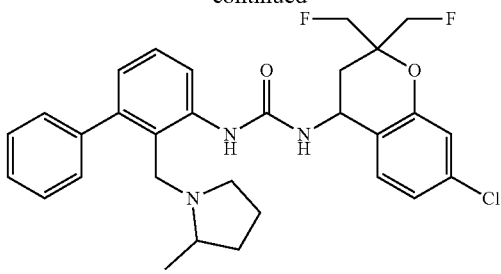

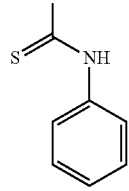
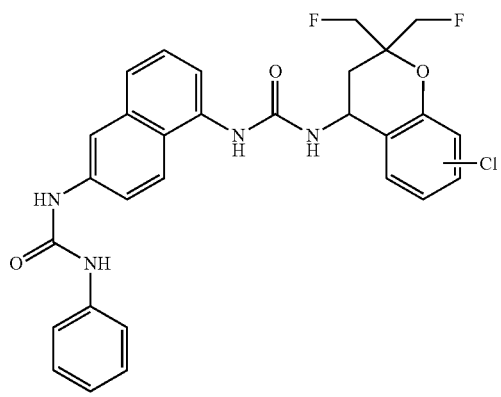

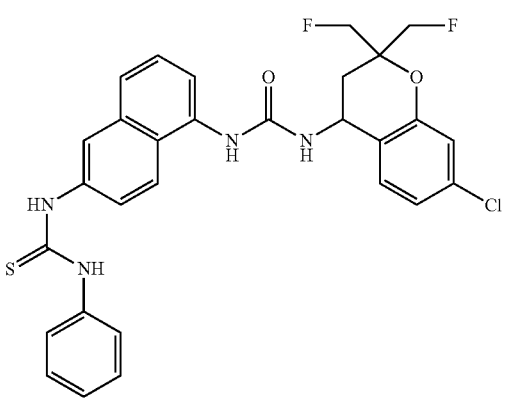 [SMILES: O=C(Nc1ccccc1)Nc1ccc2c(NC(=O)NC3CC(CF)(CF)Oc4cc(Cl)ccc43)cccc2c1]

18

-continued

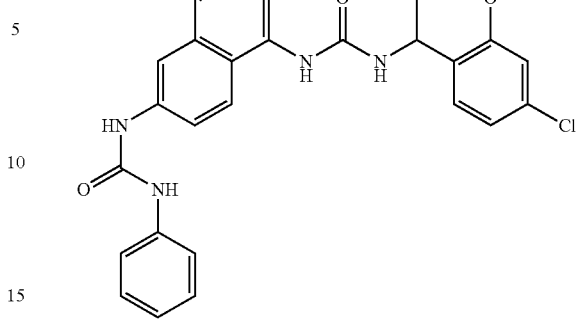

Compounds of the present disclosure also include novel compounds represented by Formula (II):

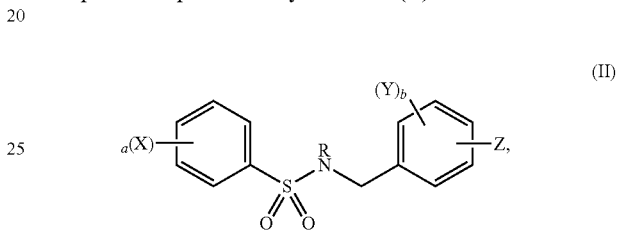

(II)

wherein:

X is independently in each instance halogen, OH, amino, COOH, CONH$_2$, SO$_3$H, PO$_3$H$_2$, CN, SH, N(R')$_2$, NO$_2$, CF$_3$C$_1$-C$_6$ perfluoroalkyl, NHC(O)—C$_1$-C$_6$ alkyl, NHC(O)—C$_1$-C$_6$ perfluoroalkyl, (C$_1$-C$_6$)alkyl, (C$_1$-C$_6$)alkoxy, (C$_1$-C$_6$)haloalkoxy, (C$_1$-C$_6$)haloalkyl, (C$_2$-C$_6$)alkenyl, (C$_2$-C$_6$)alkynyl, —NH$_2$, —NH(C$_1$-C$_6$)alkyl, —N[(C$_1$-C$_6$)alkyl]$_2$, —CN, (C$_3$-C$_8$)heteroaryl, (C$_3$-C$_8$)heterocycloalkyl, (C$_3$-C$_8$)cycloalkyl, (C$_3$-C$_8$)aryl, (C$_3$-C$_8$)heterocycloalkyl-(C$_1$-C$_6$)alkylene-, (C$_3$-C$_8$)heteroaryl-(C$_1$-C$_6$)alkylene-, (C$_3$-C$_8$)aryl(C$_1$-C$_6$)alkylene-, (C$_3$-C$_8$)aryl(C$_1$-C$_6$)alkenylene-, or (C$_1$-C$_6$)alkyl-(C$_3$-C$_8$)arylene;

Y is independently in each instance halogen, OH, amino, COOH, CONH$_2$, SO$_3$H, PO$_3$H$_2$, CN, SH, N(R')$_2$, NO$_2$, CF$_3$C$_1$-C$_6$ perfluoroalkyl, NHC(O)—C$_1$-C$_6$ alkyl, NHC(O)—C$_1$-C$_6$ perfluoroalkyl, (C$_1$-C$_6$)alkyl, (C$_1$-C$_6$)alkoxy, (C$_1$-C$_6$)haloalkoxy, (C$_1$-C$_6$)haloalkyl, (C$_2$-C$_6$)alkenyl, (C$_2$-C$_6$)alkynyl, —NH$_2$, —NH(C$_1$-C$_6$)alkyl, —N[(C$_1$-C$_6$)alkyl]$_2$, —CN, (C$_3$-C$_8$)heteroaryl, (C$_3$-C$_8$)heterocycloalkyl, (C$_3$-C$_8$)cycloalkyl, (C$_3$-C$_8$)aryl, (C$_3$-C$_8$)heterocycloalkyl-(C$_1$-C$_6$)alkylene-, (C$_3$-C$_8$)heteroaryl-(C$_1$-C$_6$)alkylene-, (C$_3$-C$_8$)aryl(C$_1$-C$_6$)alkylene-, (C$_3$-C$_8$)aryl(C$_1$-C$_6$)alkenylene-, or (C$_1$-C$_6$)alkyl-(C$_3$-C$_8$)arylene;

Z is halogen, OH, amino, COOH, CONH$_2$, SO$_3$H, PO$_3$H$_2$, CN, SH, N(R')$_2$, NO$_2$, CF$_3$C$_1$-C$_6$ perfluoroalkyl, NHC(O)—C$_1$-C$_6$ alkyl, NHC(O)—C$_1$-C$_6$ perfluoroalkyl, (C$_1$-C$_6$)alkyl, (C$_1$-C$_6$)alkoxy, (C$_1$-C$_6$)haloalkoxy, (C$_1$-C$_6$)haloalkyl, (C$_2$-C$_6$)alkenyl, (C$_2$-C$_6$)alkynyl, —NH$_2$, —NH(C$_1$-C$_6$)alkyl, —N[(C$_1$-C$_6$)alkyl]$_2$, —CN, (C$_3$-C$_8$)heteroaryl, (C$_3$-C$_8$)heterocycloalkyl, (C$_3$-C$_8$)cycloalkyl, (C$_3$-C$_8$)aryl, (C$_3$-C$_8$)heterocycloalkyl-(C$_1$-C$_6$)alkylene-, (C$_3$-C$_8$)heteroaryl-(C$_1$-C$_6$)alkylene-, (C$_3$-C$_8$)aryl(C$_1$-C$_6$)alkylene-, (C$_3$-C$_8$)aryl(C$_1$-C$_6$)alkenylene-, or (C$_1$-C$_6$)alkyl-(C$_3$-C$_8$)arylene;

R is independently in each instance H, —OH, (C$_1$-C$_6$) alkyl, (C$_1$-C$_6$) perfluoroalkyl; (C$_1$-C$_6$)alkoxy, (C$_1$-C$_6$)haloalkoxy, (C$_1$-C$_6$)haloalkyl, (C$_2$-C$_6$)alkenyl, (C$_2$-C$_6$)alkynyl, —NH$_2$, —NH(C$_1$-C$_6$)alkyl, —N[(C$_1$-C$_6$)alkyl]$_2$, —CN, ($C_3$-$C_8$)heteroaryl, ($C_3$-$C_8$)heterocycloalkyl, ($C_3$-$C_8$)cycloalkyl, ($C_3$-$C_8$)aryl, ($C_3$-$C_8$)heterocycloalkyl-($C_1$-$C_6$)alkylene-, ($C_3$-$C_8$)heteroaryl-($C_1$-$C_6$)alkylene-, ($C_3$-$C_8$)aryl($C_1$-$C_6$)alkylene-, ($C_3$-$C_8$)aryl($C_1$-$C_6$)alkenylene-, or ($C_1$-$C_6$)alkyl-($C_3$-$C_8$)arylene;

R' is independently in each instance H, —OH, ($C_1$-$C_6$) alkyl, ($C_1$-$C_6$) perfluoroalkyl; ($C_1$-$C_6$)alkoxy, ($C_1$-$C_6$)haloalkoxy, ($C_1$-$C_6$)haloalkyl, ($C_2$-$C_6$)alkenyl, ($C_2$-$C_6$)alkynyl, —$NH_2$, —NH($C_1$-$C_6$)alkyl, —N[($C_1$-$C_6$)alkyl]$_2$, —CN, ($C_3$-$C_8$)heteroaryl, ($C_3$-$C_8$)heterocycloalkyl, ($C_3$-$C_8$)cycloalkyl, ($C_3$-$C_8$)aryl, ($C_3$-$C_8$)heterocycloalkyl-($C_1$-$C_6$)alkylene-, ($C_3$-$C_8$)heteroaryl-($C_1$-$C_6$)alkylene-, ($C_3$-$C_8$)aryl($C_1$-$C_6$)alkylene-, ($C_3$-$C_8$)aryl($C_1$-$C_6$)alkenylene-, or ($C_1$-$C_6$)alkyl-($C_3$-$C_8$)arylene;

a is an integer of 0 to 5; and b is an integer of 0 to 4, wherein the alkyl moieties are optionally substituted by one or more halogen, or a pharmaceutically acceptable salt or solvate thereof.

In some embodiments, in Formula (II),

X is independently in each instance halogen, $C_1$-$C_6$ alkyl, $C_1$-$C_6$ perfluoroalkyl, NHC(O)—$C_1$-$C_6$ alkyl, NHC(O)—$C_1$-$C_6$ perfluoroalkyl;

Y is independently in each instance halogen, $C_1$-$C_6$ alkyl;

Z is N(R')$_2$, $NO_2$ or

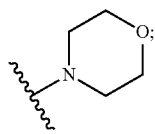

R is independently in each instance H, $C_1$-$C_6$ alkyl;

R' is independently in each instance H, $C_1$-$C_6$ alkyl, $C_1$-$C_6$ perfluoroalkyl;

a is an integer of 1 to 5; and b is an integer of 0 to 4, wherein the alkyl moieties are optionally substituted by one or more halogen, or any pharmaceutically acceptable salt or solvate thereof.

In some embodiments, the halogen is fluoro.

In some embodiments, Z is N(R')$_2$ or $NO_2$ or

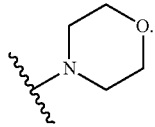 [SMILES: *N1CCOCC1]

In some embodiments, a is an integer of 1 to 5; and b is an integer of 0 to 4.

In some embodiments, the compounds of the present disclosure include novel compounds represented by Formula (IIa):

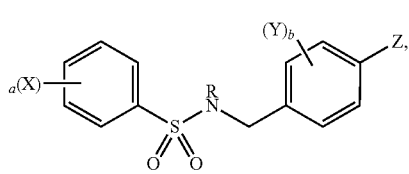

or any pharmaceutically acceptable salt or solvate thereof.

In further embodiments, the compounds of the present disclosure include novel compounds represented by Formula (IIa') or (IIa") or (IIa''') or (IIa'''') or (IIa''''')

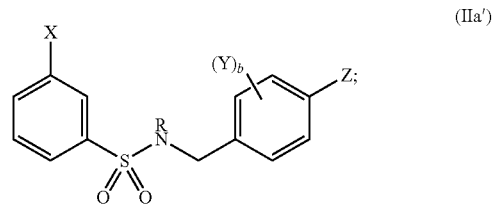

(IIa')

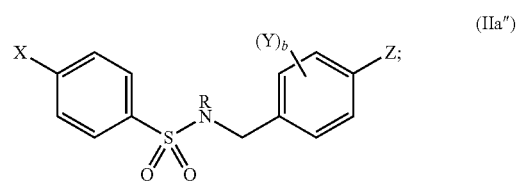

(IIa")

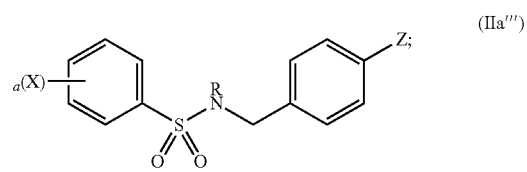

(IIa''')

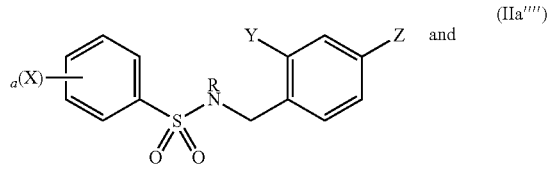

(IIa'''') and

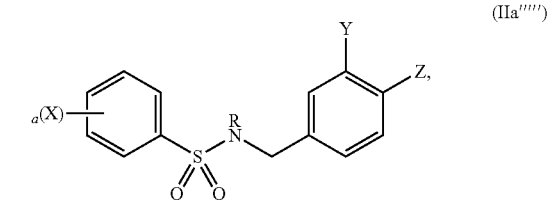

(IIa''''')

or any pharmaceutically acceptable salt or solvate thereof.

The variables of formulae (IIa), (Ia'), (Ia"), (Ia'''), (IIa''''), and (Ia''''') are the same as for Formula (II).

In some embodiments of the Formulae (I) and (II) and their sub-formulae, the $C_1$-$C_6$ alkyl is one or more of methyl, ethyl, propyl (n-, i-), butyl (n-, i-, t-, sec-), pentyl or hexyl. Preferred embodiments include methyl and ethyl. When the $C_1$-$C_6$ alkyl is substituted by one or more halogen, the embodiments include, for example, —$CH_2F$, —$CHF_2$, —$CF_3$, —$CH_2CH_2F$, —$CH_2CHF_2$, —$CH_2CF_3$, —$CHFCH_3$, —$CHFCH_2F$, —$CHFCHF_2$, —$CHFCF_3$, —$CF_2CH_3$, —$CF_2CH_2F$, —$CF_2CHF_2$, —$CF_2CF_3$.

In some embodiments, the $C_1$-$C_6$ perfluoroalkyl is a —$CF_3$ or —$CF_2CF_3$.

In some embodiments, a is 0 or 1 or 2 or 3 or 4 or 5. In a preferred embodiment, a is 1. In some embodiments, b is 0 or 1 or 2 or 3 or 4. In a preferred embodiment, b is 0 or 1.

Specific embodiments of compounds of the present invention include:
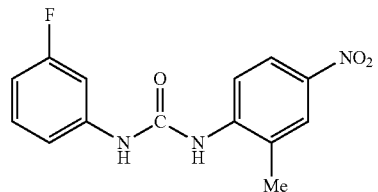
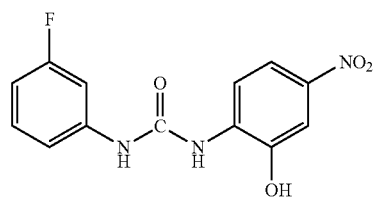
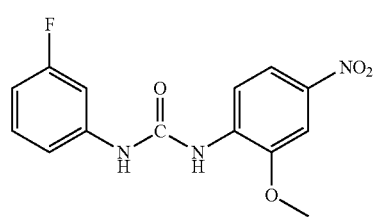
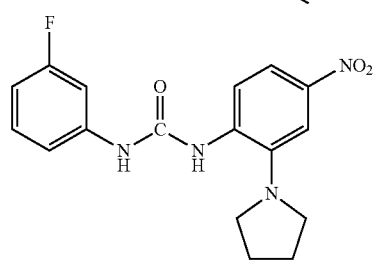
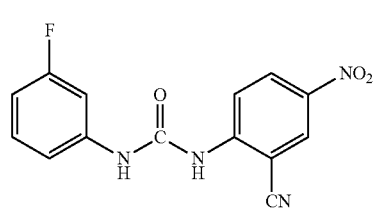
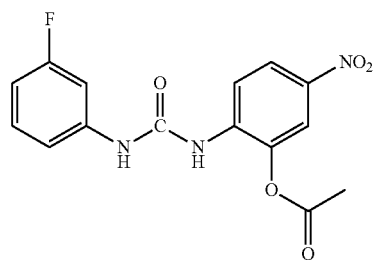
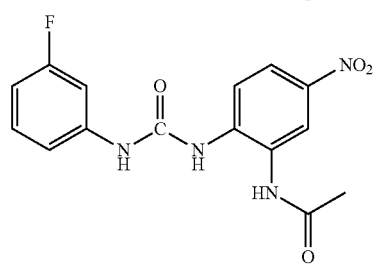
-continued
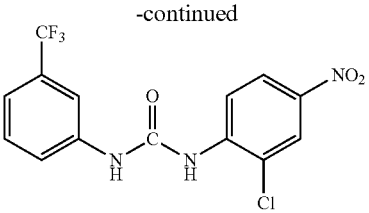
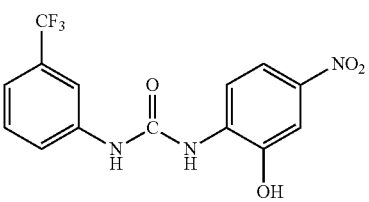
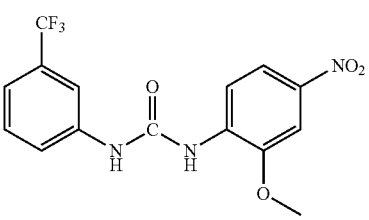
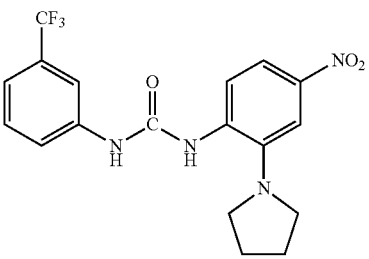
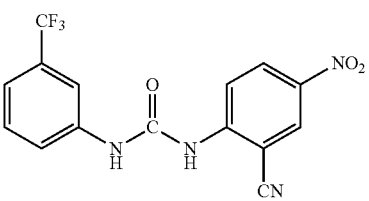
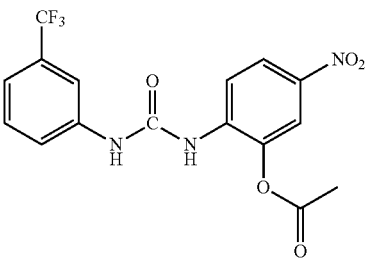
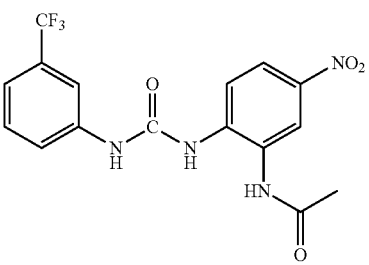

-continued

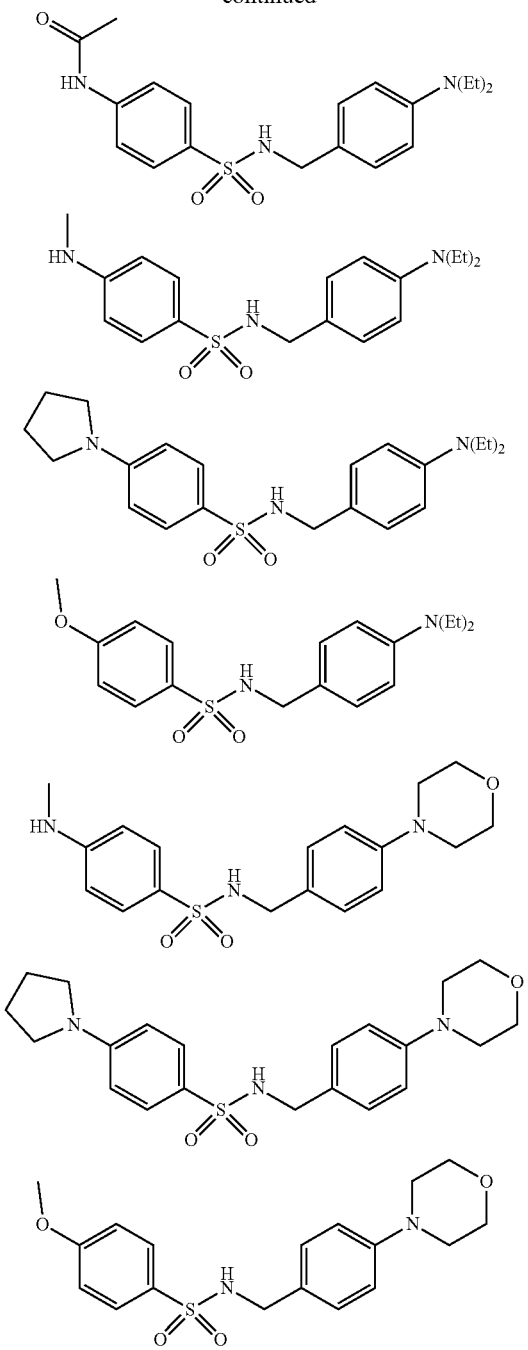

In some embodiments, the compounds of Formula (I), Formula (Ia), Formula (Ia'), Formula (Ia"), Formula (Ia'"), Formula (Ia""), Formula (Ia""') do not include the following:

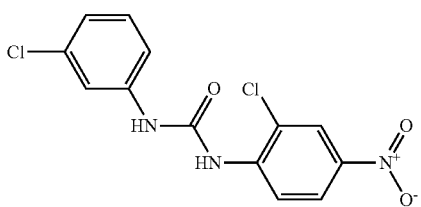

-continued

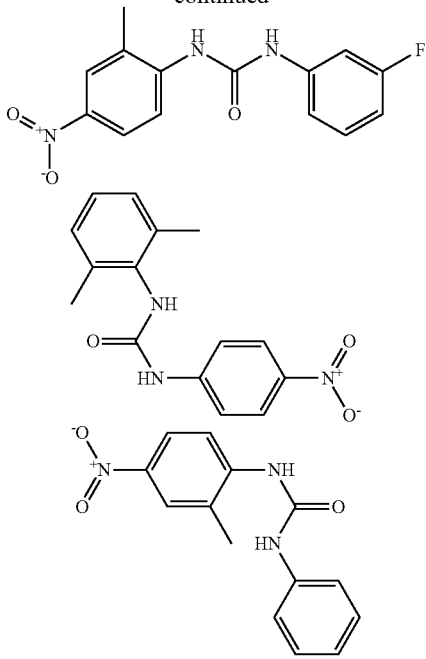

Methods of Treatment

One aspect of the present technology includes methods of antagonizing or agonizing hTRPV1 or inhibiting the activity of TRPV1 in a subject in need thereof, comprising contacting hTRPV1 with a compound or a pharmaceutically acceptable salt or solvate thereof, or administering a composition comprising such a compound or a pharmaceutically acceptable salt or solvate thereof. In some embodiments, the compound is a diarylurea compound capable of binding to a space within the TRPV1 molecule comprising (1) an upper part of the binding pocket formed by several hydrophobic residues, including Leu518, Leu547, Phe554, Leu663 and Leu670; (2) a middle consisted of several residues, including Tyr511, Met514, Thr550 and Asn551; and (3) a bottom part mainly formed by two charged residues, Glu570 and Arg557. In some embodiments, the compound binds with a Ki value of less than 5 or 4 or 3 or 2 or 1 or 0.5 M. In some embodiments, the compound is selected from the group consisting of Formula (I), Formula (Ia), Formula (Ia'), Formula (Ia"), Formula (Ia'"), Formula (Ia""), Formula (Ia""'), one of Formulae (Ia$^{6-10}$), Formula (Ib), Formula (Ib') and Formula (Ib"), Formula (Ic), Formula (Id), Formula (Ie), Formula (II), Formula (IIa), Formula (IIa'), Formula (IIa"), Formula (IIa'"), Formula (IIa""), Formula (IIa""'), and any of their sub-formulae, or any combination thereof. In one embodiment the subject is a human.

Some embodiments, include methods of antagonizing or agonizing hTRPV1 or inhibiting the activity of TRPV1 in a subject in need thereof and binding to a cannabinoid receptor 2 (CB2) and/or the C-X-C chemokine receptor 2, "CXCR2," also known as the interleukin 8 receptor beta (IL8RB), comprising contacting hTRPV1 and one of the mentioned additional receptors with a compound or a pharmaceutically acceptable salt or solvate thereof, or administering a composition comprising such a compound or a pharmaceutically acceptable salt or solvate thereof. In some embodiments, the compound is a diarylurea compound capable of binding to a space within the TRPV1 molecule comprising (1) an upper part of the binding pocket formed by several hydrophobic residues, including Leu518, Leu547, Phe554, Leu663 and Leu670; (2) a middle consisted of several residues, including Tyr511, Met514, Thr550 and Asn551; and (3) a bottom part mainly formed by two charged residues, Glu570 and Arg557 as well as the CB2 or CXCR2 receptor. In some embodiments, the compound binds with a Ki value of less than 5 or 4 or 3 or 2 or 1 or 0.5 µM. In some embodiments, the compound is selected from the group consisting of Formula (I), Formula (Ia), Formula (Ia'), Formula (Ia''), Formula (Ia'''), Formula (Ia''''), Formula (Ia'''''), one of Formulae (Ia$^{6-10}$), Formula (Ib), Formula (Ib') and Formula (Ib''), Formula (Ic), Formula (Id), Formula (Ie), Formula (II), Formula (IIa), Formula (IIa'), Formula (IIa''), Formula (IIa'''), Formula (IIa''''), Formula (IIa'''''), and any of their sub-formulae, or any combination thereof. In one embodiment the subject is a human.

Other embodiments of the present invention include a method of treating pain associated with transient receptor potential vanilloid type 1 (TRPV1) in a subject in need thereof, comprising administering to the subject an effective amount of a compound or a pharmaceutically acceptable salt or solvate thereof, or administering a composition comprising such a compound or a pharmaceutically acceptable salt or solvate thereof. In some embodiments, the compound is a diarylurea compound capable of binding to a space within the TRPV1 molecule comprising (1) an upper part of the binding pocket formed by several hydrophobic residues, including Leu518, Leu547, Phe554, Leu663 and Leu670; (2) a middle consisted of several residues, including Tyr511, Met514, Thr550 and Asn551; and (3) a bottom part was mainly formed by two charged residues, Glu570 and Arg557, such that the diarylurea compound inhibits activity of TRPV1. In some embodiments, the compound is selected from the group consisting of Formula (I), Formula (Ia), Formula (Ia'), Formula (a''), Formula (Ia'''), Formula (Ia''''), Formula (Ia'''''), one of Formulae (Ia$^{6-0}$), Formula (Ib), Formula (Ib') and Formula (Ib''), Formula (Ic), Formula (Id), Formula (Ie), Formula (II), Formula (IIa), Formula (IIa'), Formula (IIa''), Formula (IIa'''), Formula (IIa''''), Formula (IIa'''''), and any of their sub-formulae, or any combination thereof. In some embodiments, the pain associated with TRPV1 is selected from the group consisting of osteoarthritis, neuropathic pain, migraine, inflammatory bowel disease, and bone cancer pain.

In some embodiments, the method is for the treatment of acute and persistent pain, as well as inflammation, especially for the neuroinflammation. In addition, in some embodiments, the method is for the treatment of auto-immune disorders including neurodegenerative diseases and bone loss.

Compounds of Formulae I and II (including all sub-formulae), or pharmaceutically acceptable salts or solvates thereof, or a composition comprising such a compound or a pharmaceutically acceptable salt or solvate thereof, can be administered to a patient or subject in need of treatment either individually, or in combination with other therapeutic agents that have similar biological activities. For example, Formulae I and II compounds and compositions can be administered as a single dose or as multiple daily doses by a practicing medical practitioner. When combination therapy is used, however, the compound and the other therapeutic agent can be administered separately at different time intervals, or simultaneously.

Pharmaceutical formulations may include one or more Compounds of Formulae I and/or II (including all sub-formulae), or a pharmaceutically acceptable salt or solvate thereof, and a pharmaceutically acceptable carrier. In some embodiments, the composition further comprises, in accordance with accepted practices of pharmaceutical compounding, one or more additional therapeutic agents, pharmaceutically acceptable excipients, diluents, adjuvants, stabilizers, emulsifiers, preservatives, colorants, buffers, and/or flavor imparting agents.

Pharmaceutical Formulations

Pharmaceutical compositions and medicaments may be prepared by mixing one or more compounds of the invention, prodrugs thereof, pharmaceutically acceptable salts or solvates thereof, stereoisomers thereof, tautomers thereof, or solvates thereof, with pharmaceutically acceptable carriers, excipients, binders, diluents or the like to prevent and treat disorders associated with TRPV1 or cannabinoid receptors.

The compounds and compositions of the invention may be used to prepare formulations and medicaments that prevent or treat a variety of disorders associated with TRPV1 or cannabinoid receptors, as described herein. For example, disorders and diseases such as obesity, smoking addiction, cardimetabolic risk factors, and other disorder and diseases associated with the central nervous system can be treated using the methods, compounds, and compositions of the invention. Such compositions can be in any pharmaceutically acceptable form, such as but not limited to in the form of, for example, granules, powders, tablets, capsules, syrup, suppositories, injections, emulsions, elixirs, suspensions or solutions. The compositions can be formulated for any pharmaceutically acceptable route of administration, such as for example, by oral, parenteral, pulmonary, topical, rectal, nasal, vaginal administration, or via implanted reservoir. Parenteral or systemic administration includes, but is not limited to, subcutaneous, intravenous, intraperitoneally, intramuscular, intra-articular, intrasynovial, intrasternal, intrathecal, intralesional and intracranial injections. The following dosage forms are given by way of example and should not be construed as limiting the invention.

Pharmaceutically acceptable salts of the invention compounds are considered within the scope of the present invention. The compounds of the invention have a number of basic nitrogen groups, and as such, pharmaceutically acceptable salts can be formed with inorganic acids (such as hydrochloric acid, hydroboric acid, nitric acid, sulfuric acid, and phosphoric acid), organic acids (e.g. formic acid, acetic acid, trifluoroacetic acid, fumaric acid, oxalic acid, tartaric acid, lactic acid, maleic acid, citric acid, succinic acid, malic acid, methanesulfonic acid, benzenesulfonic acid, and p-toluenesulfonic acid) or acidic amino acids (such as aspartic acid and glutamic acid). The compounds of the present invention may have acidic substituent groups, and in such cases, it can form salts with metals, such as alkali and earth alkali metals (e.g. Na$^+$, Li$^-$, K$^+$, Ca$^{2+}$, Mg$^{2+}$, Zn$^{2+}$), organic amines (e.g. ammonia, trimethylamine, triethylamine, pyridine, picoline, ethanolamine, diethanolamine, triethanolamine) or basic amino acids (e.g. arginine, lysine and ornithine).

Certain compounds within the scope of the invention are derivatives referred to as prodrugs. The expression "prodrug" denotes a derivative of a known direct acting drug, e.g. esters and amides, which derivative has enhanced delivery characteristics and therapeutic value as compared to the drug, and is transformed into the active drug by an enzymatic or chemical process; see Notari, R. E., "Theory and Practice of Prodrug Kinetics," *Methods in Enzymology*, 112: 309-23 (1985); Bodor, N., "Novel Approaches in Prodrug Design," *Drugs of the Future*, 6: 165-82 (1981); and Bundgaard, H., "Design of Prodrugs: Bioreversible-Derivatives for Various Functional Groups and Chemical Entities," in DESIGN OF PRODRUGS (H. Bundgaard, ed.), Elsevier (1985), and Goodman and Gilmans, *The Pharmacological Basis Of Therapeutics,* 8th ed., McGraw-Hill (1992).

For oral, buccal, and sublingual administration, powders, suspensions, granules, tablets, pills, capsules, gelcaps, and caplets are acceptable as solid dosage forms. These can be prepared, for example, by mixing one or more compounds of the present invention, or pharmaceutically acceptable salts or tautomers thereof, with at least one additive such as a starch or other additive. Suitable additives include any pharmaceutically acceptable excipient, including but not limited to sucrose, lactose, cellulose sugar, mannitol, maltitol, dextran, starch, agar, alginates, chitins, chitosans, pectins, tragacanth gum, gum arabic, gelatins, collagens, casein, albumin, synthetic or semi-synthetic polymers or glycerides. Optionally, oral dosage forms can comprise other ingredients to aid in administration, such as an inactive diluent, or lubricants such as magnesium stearate, or preservatives such as paraben or sorbic acid, or anti-oxidants such as ascorbic acid, tocopherol or cysteine, a disintegrating agent, binders, thickeners, buffers, sweeteners, flavoring agents or perfuming agents. Tablets and pills may be further treated with suitable coating materials known in the art.

Definitions

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely", "only" and the like in connection with the recitation of claim elements, or use of a "negative" limitation.

As used herein, the term "about" will be understood by persons of ordinary skill in the art and will vary to some extent depending upon the context in which it is used. If there are uses of the term which are not clear to persons of ordinary skill in the art given the context in which it is used, "about" will mean up to plus or minus 10% of the particular term.

By "pharmaceutically acceptable" is meant a material that is not biologically or otherwise undesirable, i.e., the material may be incorporated into a pharmaceutical composition administered to a patient without causing any undesirable biological effects or interacting in a deleterious manner with any of the other components of the composition in which it is contained. When the term "pharmaceutically acceptable" is used to refer to a pharmaceutical carrier or excipient, it is implied that the carrier or excipient has met the required standards of toxicological and manufacturing testing or that it is included on the Inactive Ingredient Guide prepared by the U.S. and Drug administration.

By "patient" is meant any animal for which treatment is desirable. Patients may be mammals, and typically, as used herein, a patient is a human individual.

The term "pharmaceutically acceptable salt," as used herein, represents salts or zwitterionic forms of the compounds of the present invention which are water or oil-soluble or dispersible; which are suitable for treatment of diseases without undue toxicity, irritation, and allergic-response; which are commensurate with a reasonable benefit/risk ratio; and which are effective for their intended use. The salts can be prepared during the final isolation and purification of the compounds or separately by reacting the appropriate compound in the form of the free base with a suitable acid. Representative acid addition salts include acetate, adipate, alginate, L-ascorbate, aspartate, benzoate, benzenesulfonate (besylate), bisulfate, butyrate, camphorate, camphorsulfonate, citrate, digluconate, formate, fumarate, gentisate, glutarate, glycerophosphate, glycolate, hemisulfate, heptanoate, hexanoate, hippurate, hydrochloride, hydrobromide, hydroiodide, 2-hydroxyethansulfonate (isethionate), lactate, maleate, malonate, DL-mandelate, mesitylenesulfonate, methanesulfonate, naphthylenesulfonate, nicotinate, 2-naphthalenesulfonate, oxalate, pamoate, pectinate, persulfate, 3-phenylproprionate, phosphonate, picrate, pivalate, propionate, pyroglutamate, succinate, sulfonate, tartrate, L-tartrate, trichloroacetate, trifluoroacetate, phosphate, glutamate, bicarbonate, para-toluenesulfonate (p-tosylate), and undecanoate. Also, basic groups in the compounds of the present invention can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form pharmaceutically acceptable addition salts include inorganic acids such as hydrochloric, hydrobromic, sulfuric, and phosphoric, and organic acids such as oxalic, maleic, succinic, and citric. Salts can also be formed by coordination of the compounds with an alkali metal or alkaline earth ion. Hence, the present invention contemplates sodium, potassium, magnesium, and calcium salts of the compounds of the compounds of the present invention and the like.

The term "solvates" is used in its broadest sense. For example, the term solvates includes hydrates formed when a compound of the present invention contains one or more bound water molecules.

Certain ranges are presented herein with numerical values being preceded by the term "about". The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

This invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

WORKING EXAMPLES

The present technology is further illustrated by the following examples, which should not be construed as limiting in any way.

Binding Competition Assay and $Ca^{2+}$ Uptake Assay.

Materials.

[$^3$H]Resiniferatoxin ([$^3$H]RTX, 37 Ci/mmol) was provided by Perkin Elmer Life Sciences (Boston, Mass.). Radioactive calcium (Ca-45, specific activity 5-30 Ci/g) was obtained from Perkin Elmer. Nonradioactive RTX was obtained from LC laboratories (Waltham, Mass.). Capsaicin was provided by Sigma-Aldrich (St. Louis, Mo.).

Stable hTRPV1 Expression Cell Line Subculture.

Tet-On induced CHO-hTRPV1 cells were cultured in maintaining medium (F12 supplemented with 10% TET-free FBS [Atlanta Biologicals, GA], 25 mM HEPES, 10 µg/ml blasticidin and 250 µg/ml geneticin (all from Invitrogen Life Sciences; Grand Island, N.Y.). TRPV1 protein was induced with induction medium (F12 supplemented with 10% FBS, 25 mM HEPES, and 1 µg/ml tetracycline) as described below for ligand binding and Ca uptake measurements.

RTX Competition Binding Assay.

Binding studies with [$^3$H]RTX were carried out as follows. The binding assay mixtures were prepared in 1.5 ml centrifuge tubes and consisted of a fixed concentration (approximately 2 nM) of [$^3$H]RTX (37 Ci/mmol specific activity, PerkinElmer Life Sciences), various concentrations of competing ligands, and 100 g protein of membranes from induced CHO-hTRPV1 expressing cells (approximately 1-3×10$^6$ cells) in Dulbecco's phosphate buffered saline (DPBS, with $Ca^{2+}$ & $Mg^{2+}$) for a total volume of 350 µl. The assay mix contained bovine serum albumin at a final concentration of 0.25 mg/ml (Cohn fraction V; Sigma-Aldrich, St. Louis, Mo.). In each set of experiments, nonspecific binding were determined in the presence of 200 nM nonradioactive RTX. The binding reaction was initiated by placing the assay mixture in a 37° C. shaking water bath for 60 minutes (~30 rpm). The assay mixture was then chilled on ice for 2-3 min before adding 100 µl of $\alpha_1$-acid glycoprotein (2 mg/ml; Sigma-Aldrich) and mixed thoroughly. The tubes were kept on ice for an additional 10 min. The bound and free ligands were then separated by centrifugation (12,200 rpm for 15 minutes) in a Beckman Coulter centrifuge Allegra 21R. 200 µl of supernatant was collected for determination of free ligand. The remainder was removed by aspiration. The bottom portion of the tubes containing the membranes was cut off and bound radioactivity determined. Radioactivity was measured by scintillation counting. Data were analyzed using GraphPad Prism. $K_i$ values for compounds were determined by competition for binding of [$^3$H]RTX to the hTRPV1 and represent the mean SEM of triplicate binding curves. In each curve, triplicate determinations were performed at each ligand concentration.

Calcium Uptake Assays.

CHO-hTRPV1 cells were plated in 24-well plates, reaching 40 to 60% confluence in maintaining medium after 24 hours. The cells were washed once with Dulbecco's phosphate buffered saline (DPBS; Invitrogen, Grand Island, N.Y.) to remove antibiotics, and fresh medium with tetracycline (inducing medium) was added to induce TRPV1 expression. Experiments were done approximately 24 hours after induction. The cells were at least 90% confluent at the time of the assays.

For agonist $Ca^{2+}$ uptake assays, the inducing medium was aspirated and replaced by DMEM (supplemented with bovine serum albumin (0.25 mg/mL), $Ca^{2+}$ (37 kBq/mL), and 100 µl of increasing concentrations of the non-radioactive ligand for a total volume of 400 µl/well. The cells were incubated for 5 min in a water bath at 37° C. For uptake measurements by a full agonist, a saturating concentration of capsaicin (3000 nM) was used as a positive control. Immediately after incubation, the assay medium was aspirated and the cells were washed twice with ice cold DPBS (no $Ca^{2+}$ & $Mg^{2+}$). The cells were then lysed in radioimmunoprecipitation assay buffer (50 mM Tris-Cl pH 7.5, 150 mM NaCl, 1% Triton X-100, 1% SDS, and 1% sodium deoxycholate; 400 µL/well) for at least 40 min on a shaker. Aliquots (300 µL) of the cell lysates were counted in a liquid scintillation counter. Background uptake was determined in the absence of either compound or capsaicin. For the antagonism assays, capsaicin (30 nM) was included along with increasing concentrations of the ligand being evaluated. The cells were incubated for 5 min in a water bath at 37° C. Immediately after incubation, the assay medium was aspirated and the cells were washed twice with ice-cold DPBS (no $Ca^{2-}$ & $Mg^{2+}$). The cells were then lysed in radioimmunoprecipitation assay buffer for at least 40 min on a shaker. Aliquots of the cell lysate were counted in a liquid scintillation counter. Triplicate points at each concentration of ligand were determined in each experiment. Compounds were initially screened at a concentration of 30 µM. Compounds showing greater than 10% agonism/antagonism were evaluated in triplicate experiments. As indicated, full dose response curves for compounds showing activity were performed at least three times. Data was analyzed using GraphPad Prism.

Example 1. Synthesis of Compound 1

The purpose of this example as to synthesize Compound 1, the structure of which is shown below:

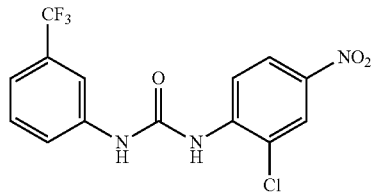

31

-continued

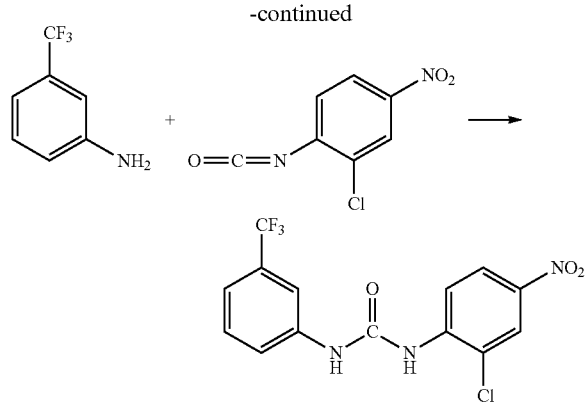

Taking 2-chloro-1-isocyanato-4-nitrobenzene and 3-(trifluoromethyl)aniline as staring materials, compound 1 was synthesized using the same method as compound 2.

This compound yielded Ki values for capsaicin antagonism of 2.60±0.62 μM. It likewise inhibited [3H]RTX binding to hTRPV1 with Ki value of 1.11±0.21 μM.

Example 2. Synthesis of Compound 2

The purpose of this example as to synthesize Compound 2, the structure of which is shown below:

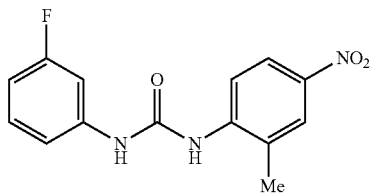 [SMILES: Cc1cc([N+](=O)[O-])ccc1NC(=O)Nc1cccc(F)c1]

Compound 2 was synthesized by the method of the following Scheme.

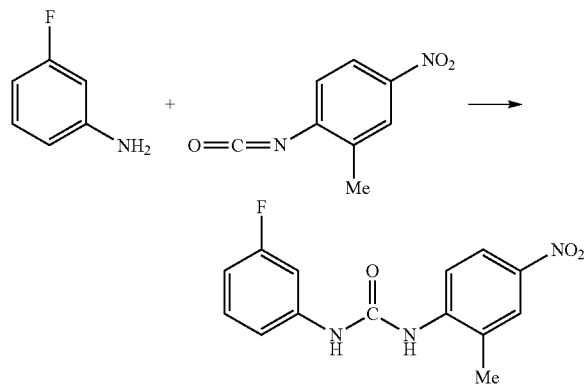

General Procedure of Coupling Reaction Between Isocyanate and Amine.

1-isocyanato-2-methyl-4-nitrobenzene (1.6 mmol, 1 eqv.) was dissolved in dichloromethane (10 mL). 3-fluoroaniline (2.4 mmol, 1.5 eqv) was added, followed by triethylamine (3.6 mmol, 2.25 eqv) and the resulting mixture was stirred overnight at room temperature. A precipitate was formed, filtered and washed with dichloromethane. The solid par-

32 ticles were purified with flash column chromatography utilizing ethyl acetate/petroleum ether (1:2). The target compound was obtained as off-white solid (100 mg, yield: 34%).
$^1$H NMR (400 MHz, DMSO-d6, ppm) δ 9.60 (s, 1H), 8.44 (s, 1H), 8.34 (d, J=8.80 Hz, 1H), 8.14-8.08 (m, 2H), 7.54 (d, J=11.60 Hz, 1H), 7.37-7.35 (m, 1H), 7.15-7.13 (m, 1H), 6.86-6.85 (m, 1H), 2.38 (s, 3H). LC-MS (ESI, m/z): 290.0 (M+H)$^+$. This compound yielded Ki values for capsaicin antagonism of 4.50±0.88 M. It likewise inhibited [3H]RTX binding to hTRPV1 with Ki value of 5.20±0.32 μM.

Example 3. Synthesis of Compound 3

The purpose of this example as to synthesize Compound 3, the structure of which is shown below:

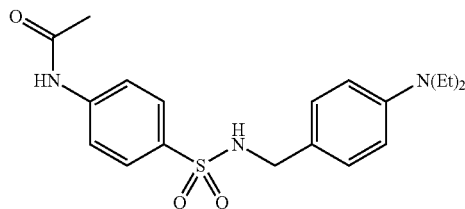

4-Acetamidobenzene-1-sulfonyl chloride (466 mg, 2.0 mmol) and 4-(aminomethyl)-N,N-diethylaniline (356 mg, 2.0 mmol) were dissolved in 10 mL of water and 5 mL of dimethylformamide. The mixture was added K$_2$CO$_3$ (414 mg, 3.0 mmol) and stirred at room temperature for 12 h. The precipitated solid was filtered, washed with water, and dried in vacuo to obtain the crude product, which was recrystallized in ethanol to prepare the final compound N-(4-(N-(4-(diethylamino)benzyl)sulfamoyl)phenyl)acetamide (453 mg, 60%).
$^1$H NMR (400 MHz, DMSO-d6) δ 10.28 (s, 1H), 7.69-7.75 (m, 5H), 6.97 (d, J=8.4 Hz, 2H), 6.52 (d, J=8.4 Hz, 2H), 3.79 (d, J=6.0 Hz, 2H), 3.28-3.35 (m, 4H), 2.09 (s, 3H), 1.05 (t, J=6.8 Hz, 6H). LC-MS (ESI): m/z 376.1 (M+H)$^+$. It antagonized capsaicin stimulation of hTRPV1 by 12.7±1.0% at 30 μM.

Example 4. The Sequence Alignment Between hTRPV1 and rTRPV1

The purpose of this example was to determine the sequence alignment between human TRPV1 (hTRPV1) and rat TRPV1 (rTRPV1), as shown in FIG. 1.

The whole sequence identity between hTRPV1 and rTRPV1 was 85.7%. We used the structure of rTRPV1-capsaicin (PDB entry: 3JSR, EM resolution: 4.2 Å) to construct the 3D structures of hTRPV1. The intact sequence of hTRPV1 (Q8NER1, 839 residues for one monomer) was downloaded from the UniProtKB/Swiss-Prot (http://www.uniprot.org/uniprot/).

We truncated some residues before Leu112 for the N terminus and some residues after Lys719 for the C terminus. We also truncated 24 residues from Asn604 to Ser627. This truncation was necessary because the corresponding residues were unsolved in the structures of rTRPV1. Therefore, the generated sequence was from Leu112 to Lys603 and from Tyr628 to Lys719 (584 residues for one monomer). We connected Lys603 and Tyr628 to generate a continuous polypeptide sequence. We then aligned the sequence and built the homology model based on this hTRPV1 sequence by using our reported protocol.

Example 5. Ramachandran Plots of hTRPV1 Model

The purpose of this example was to generate Ramachandran plots of hTRPV1.

Ramachandran plots of hTRPV1 model constructed by rTRPV1 95.5% (554/580) of all residues were in favored regions. 99.1% (575/580) of all residues were in allowed regions. There were 5 outliers (phi, psi): Glu250 (56.0, −24.3), Leu385 (88.0, 72.8), Thr407 (88.0, −19.7), Asp459 (22.4, −126.2), Pro462 (−28.9, −68.7).

After obtaining the 3D structures, SYBYL-X 1.3 was used for the energy minimizations. SYBYL-X 1.3, Tripos International, 1699 South Hanley Rd., St. Louis, Mo., 63144, USA. 2010. ProSA-web Z-scores and ProCheck Ramachandran plots were used for structural stereochemical evaluation of the hTRPV1 models.

Example 6. Detailed Binding Modes of Six Antagonists with hTRPV1

The purpose of this example was to determine detailed binding modes of six antagonists with hTRPV1.

Most residues involved in the binding pocket had similar roles for the recognition of antagonists. (1) Ser512 (not shown), Arg557, and Glu570 formed a hydrophilic pocket that interacted with the polar/charged groups of the antagonists. (2) Thr550 and/or Tyr511 also formed strong hydrogen bonds with these 8 compounds. (3) Several hydrophobic residues formed strong hydrophobic interactions with all these antagonists, including Met514, Leu515 (not shown), Leu518, Leu547, Ala666 (not shown), and Leu670. The agonists and antagonists therefore shared the same binding pocket and similar binding interactions, which were congruent with the findings of GPCRs.

Example 7. Determination of Four Allosteric Binding Pockets in Tetramer hTRPV1 Model The purpose of this example was to determine four allosteric binding pockets in a tetramer hTRPV1 model.

Each predicted binding pocket was formed by five transmembrane domains from two adjacent monomers, including S3, S4, S4-S5 linker, S5, and S6. An important observation was that the binding pockets of hTRPV1 differed from the traditional orthosteric binding site because they were exposed to the lipids. Our MD simulation showed that both AMG9810 (antagonist) and RTX (agonist) were close to the lipid molecules (~5.4 Å and 5.7 Å for these two compounds, respectively). All the results showed that these were allosteric binding pockets. Our findings were congruent with the reports by Julius and co-workers. Liao, M.; Cao, E.; Julius, D.; Cheng, Y. Structure of the TRPV1 Ion Channel Determined by Electron Cryo-Microscopy. *Nature* 2013, 504, 107-112. In their apo structure of rTRPV1, they observed some density in the same site as the agonists, possibly correspond ng to a detergent molecule or lipid. They suggested that this binding site of ligands was in exchange with lipid molecules. This hypothesis was supported by experimental data, suggesting that TRPV1 can be activated by lipophilic or lipid molecules, such as diacylglycerols and anandamide. Consistently, some studies already showed a shared binding site for RTX and anandamide and partial activation of TRPV1 by diacylglycerol.

Example 8. In Vitro Testing of Compound

For an initial evaluation of the utility of the model for identifying novel structures with hTRPV1 activity, a panel of several in-house compounds was examined. The in-house compounds were selected on the basis of the docking score (higher than 8.0). Of all the in-house compounds, one (XIE1-203Y) antagonized capsaicin stimulation of hTRPV1 by 12.7±1.0% at 30 µM. Among the other compounds, 2 gave 98.2±2.7% (compound 1) and 79.9±4.9% (compound 2) inhibition at 30 M. These compounds yielded $K_i$ values for capsaicin antagonism of 2.60±0.62 (compound 1) and 4.50±0.88 (compound 2) µM, respectively. They likewise inhibited [$^3$H]RTX binding to hTRPV1 with $K_i$ values of 1.11±0.21 and 5.20±0.32 M, respectively.

TABLE 1

TRPV1 inhibitors.

| Compound ID | Structure | LogP | MW | $^aK_i$ (µM) (or % inhibition at 30 µM) |
|---|---|---|---|---|
| 1 | (structure shown) | 4.09 | 359.68 | 2.57 ± 0.62 (92.2 ± 2.7%) |
| 2 | (structure shown) | 3.04 | 289.27 | 4.52 ± 0.88 (79.9 ± 4.9%) |

TABLE 1-continued

TRPV1 inhibitors.

| Compound ID | Structure | LogP | MW | $^a K_i$ (μM) (or % inhibition at 30 μM) |
|---|---|---|---|---|
| 3 | 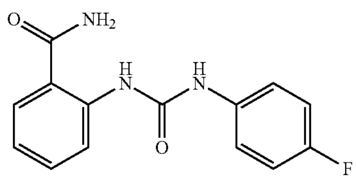 [SMILES: NC(=O)c1ccccc1NC(=O)Nc1ccc(F)cc1] | 1.58 | 273.27 | 32 ± 8% |
| 4 | 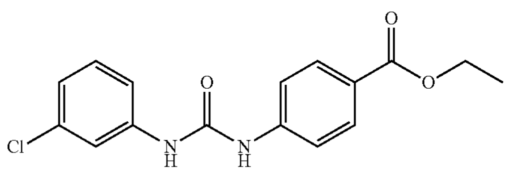 [SMILES: CCOC(=O)c1ccc(NC(=O)Nc2cccc(Cl)c2)cc1] | 3.23 | 318.76 | 11.7 ± 1.3 (64.5 ± 7.3%) |
| 5[b] | 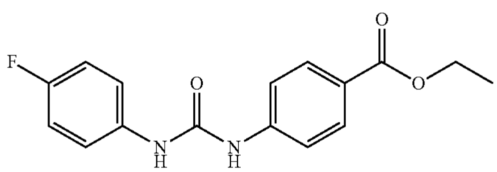 [SMILES: CCOC(=O)c1ccc(NC(=O)Nc2ccc(F)cc2)cc1] | 2.83 | 302.31 | 2.84 ± 0.21[b] (55.7 ± 7.8% agonism) |
| 6 | 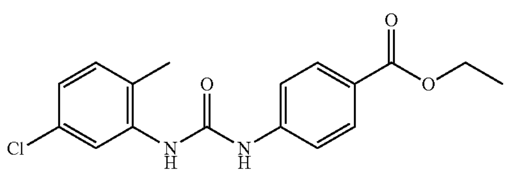 [SMILES: CCOC(=O)c1ccc(NC(=O)Nc2cc(Cl)ccc2C)cc1] | 3.72 | 332.78 | 34 ± 7% |
| 7 | 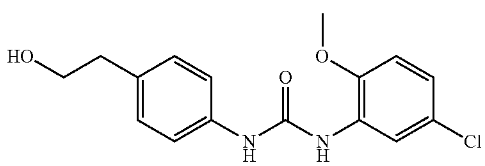 [SMILES: COc1ccc(Cl)cc1NC(=O)Nc1ccc(CCO)cc1] | 2.65 | 320.77 | 33 ± 7% |
| 8 | 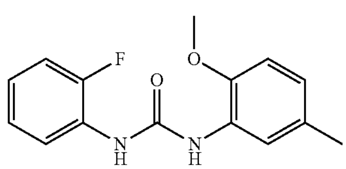 [SMILES: COc1ccc(C)cc1NC(=O)Nc1ccccc1F] | 3.03 | 274.30 | 28 ± 6% |
| 9 | 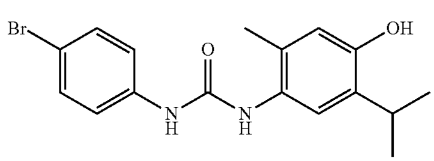 [SMILES: Cc1cc(O)c(C(C)C)cc1NC(=O)Nc1ccc(Br)cc1] | 4.67 | 363.26 | 27 ± 14% |
| 10 | 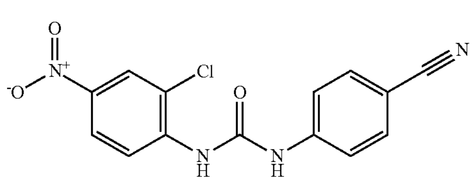 | 2.62 | 316.70 | 35 ± 5% |

TABLE 1-continued

TRPV1 inhibitors.

| Compound ID | Structure | LogP | MW | $K_i$ (μM) (or % inhibition at 30 μM) |
|---|---|---|---|---|
| 11 | 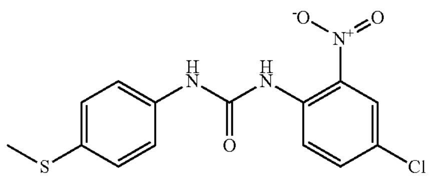 | 3.93 | 337.78 | 3.7 ± 1.7 (61 ± 18%) |
| 12 | 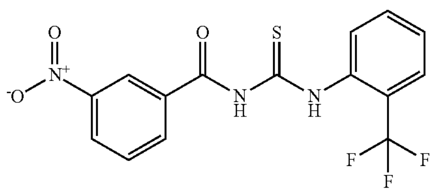 | 3.76 | 369.32 | 23 ± 12% |
| 13 | 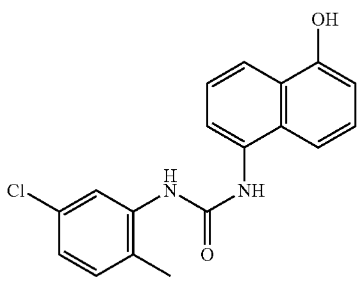 [SMILES: Cc1ccc(Cl)cc1NC(=O)Nc1cccc2c(O)cccc12] | 4.17 | 326.78 | 3.7 ± 1.0 (72 ± 18%) |
| 14 | 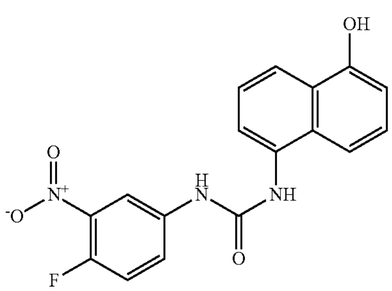 | 3.36 | 341.30 | 0.47 ± 0.18 (100 ± 0%) |
| 15 | 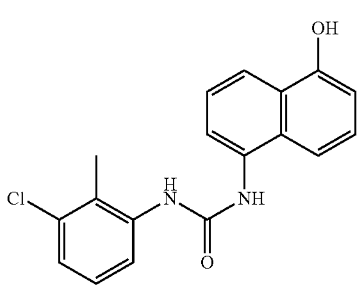 [SMILES: Cc1c(Cl)cccc1NC(=O)Nc1cccc2c(O)cccc12] | 4.17 | 326.18 | 0.49 ± 0.14 (99.6 ± 0.40%) |
| 16 | 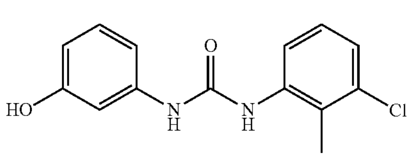 [SMILES: Cc1c(Cl)cccc1NC(=O)Nc1cccc(O)c1] | 3.17 | 276.72 | 0.56 ± 0.16 (100 ± 0%) |

TABLE 1-continued

TRPV1 inhibitors.

| Compound ID | Structure | LogP | MW | $^a$K$_i$ (μM) (or % inhibition at 30 μM) |
|---|---|---|---|---|
| 17 | (structure: phenanthrenequinone with nitro oxide and two Br substituents) | 3.23 | 411.01 | 2.15 ± 0.72 (66 ± 11%) |
| 18 | (structure: benzamide with Cl, CF$_3$, and F substituents) | 4.48 | 317.67 | 7.0 ± 2.0 (51.8 ± 6.6%) |

$^a$K$_i$ values for capsaicin antagonism. For weak compounds, the % inhibition at 30 μM is given.
$^b$Compound 5 was identified as a partial agonist. The value listed is for agonism

Example 9. Binding at the Cannabinoid Receptor 2 (CB2)

The compounds were also tested for activity in the CB2 receptor, and showed that the binding curve for compound 15 with a Ki value of 1.39 μM at CB2, while 14 and 16 showed weak binding activity with a K$_i$ value of 15.9 M and 12.2 μM.

What is claimed is:

1. A compound represented by Formula (I):

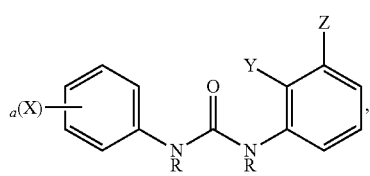

(I)

wherein:

two of X are present on adjacent atoms, and together form a five or six-membered aryl, heteroaryl, heterocyclic or cyclic ring that is optionally substituted by one or more halogen, OH, amino, COOH, CONH$_2$, SO$_3$H, PO$_3$H$_2$, CN, SH, N(R')$_2$, NO$_2$, CF$_3$C$_1$-C$_6$ perfluoroalkyl, NHC(O)—C$_1$-C$_6$ alkyl, NHC(O)—C$_1$-C$_6$ perfluoroalkyl, (C$_1$-C$_6$)alkyl, (C$_1$-C$_6$)alkoxy, (C$_1$-C$_6$)haloalkoxy, (C$_1$-C$_6$)haloalkyl, (C$_2$-C$_6$)alkenyl, (C$_2$-C$_6$)alkynyl, —NH$_2$, —NH(C$_1$-C$_6$)alkyl, —N[(C$_1$-C$_6$)alkyl]$_2$, —CN, (C$_3$-C$_8$)heteroaryl, (C$_3$-C$_8$)heterocycloalkyl, (C$_3$-C$_8$)cycloalkyl, $(C_3-C_8)$aryl, $(C_3-C_8)$heterocycloalkyl-$(C_1-C_6)$alkylene-, $(C_3-C_8)$heteroaryl-$(C_1-C_6)$alkylene-, $(C_3-C_8)$aryl$(C_1-C_6)$alkylene-, $(C_3-C_8)$aryl$(C_1-C_6)$alkenylene-, or $(C_1-C_6)$alkyl-$(C_3-C_8)$arylene;

Y is halogen, CN, $NO_2$, $CF_3C_1-C_6$ perfluoroalkyl, $(C_1-C_6)$alkyl, $(C_1-C_6)$alkoxy, $(C_1-C_6)$haloalkoxy, $(C_1-C_6)$haloalkyl, $(C_2-C_6)$alkenyl, $(C_2-C_6)$alkynyl, —N[$(C_1-C_6)$alkyl]$_2$, $(C_3-C_8)$cycloalkyl, $(C_3-C_8)$aryl, $(C_3-C_8)$aryl$(C_1-C_6)$alkylene-, $(C_3-C_8)$aryl$(C_1-C_6)$alkenylene-, or $(C_1-C_6)$alkyl-$(C_3-C_8)$arylene;

Z is OH, amino, COOH, $CONH_2$, $SO_3H$, $PO_3H_2$, CN, SH, N(R')$_2$, $NO_2$, $CF_3C_1-C_6$ perfluoroalkyl, NHC(O)—$C_1-C_6$ alkyl, NHC(O)—$C_1-C_6$ perfluoroalkyl, $(C_1-C_6)$alkyl, $(C_1-C_6)$alkoxy, $(C_1-C_6)$haloalkoxy, $(C_1-C_6)$haloalkyl, $(C_2-C_6)$alkenyl, $(C_2-C_6)$alkynyl, —$NH_2$, —NH$(C_1-C_6)$alkyl, —N[$(C_1-C_6)$alkyl]$_2$, —CN, $(C_3-C_8)$heteroaryl, $(C_3-C_8)$heterocycloalkyl, $(C_3-C_8)$cycloalkyl, $(C_3-C_8)$aryl, $(C_3-C_8)$heterocycloalkyl-$(C_1-C_6)$alkylene-, $(C_3-C_8)$heteroaryl-$(C_1-C_6)$alkylene-, $(C_3-C_8)$aryl$(C_1-C_6)$alkylene-, $(C_3-C_8)$aryl$(C_1-C_6)$alkenylene-, or $(C_1-C_6)$alkyl-$(C_3-C_8)$arylene;

R is independently in each instance H, —OH, $(C_1-C_6)$alkyl, $(C_1-C_6)$ perfluoroalkyl, $(C_1-C_6)$alkoxy, $(C_1-C_6)$haloalkoxy, $(C_1-C_6)$haloalkyl, $(C_2-C_6)$alkenyl, $(C_2-C_6)$alkynyl, —$NH_2$, —NH$(C_1-C_6)$alkyl, —N[$(C_1-C_6)$alkyl]$_2$, —CN, $(C_3-C_8)$heteroaryl, $(C_3-C_8)$heterocycloalkyl, $(C_3-C_8)$cycloalkyl, $(C_3-C_8)$aryl, $(C_3-C_8)$heterocycloalkyl-$(C_1-C_6)$alkylene-, $(C_3-C_8)$heteroaryl-$(C_1-C_6)$alkylene-, $(C_3-C_8)$aryl$(C_1-C_6)$alkylene-, $(C_3-C_8)$aryl$(C_1-C_6)$alkenylene-, or $(C_1-C_6)$alkyl-$(C_3-C_8)$arylene;

R' is independently in each instance H, —OH, $(C_1-C_6)$alkyl, $(C_1-C_6)$ perfluoroalkyl, $(C_1-C_6)$alkoxy, $(C_1-C_6)$haloalkoxy, $(C_1-C_6)$haloalkyl, $(C_2-C_6)$alkenyl, $(C_2-C_6)$alkynyl, —$NH_2$, —NH$(C_1-C_6)$alkyl, —N[$(C_1-C_6)$alkyl]$_2$, —CN, $(C_3-C_8)$heteroaryl, $(C_3-C_8)$heterocycloalkyl, $(C_3-C_8)$cycloalkyl, $(C_3-C_8)$aryl, $(C_3-C_8)$heterocycloalkyl-$(C_1-C_6)$alkylene-, $(C_3-C_8)$heteroaryl-$(C_1-C_6)$alkylene-, $(C_3-C_8)$aryl$(C_1-C_6)$alkylene-, $(C_3-C_8)$aryl$(C_1-C_6)$alkenylene-, or $(C_1-C_6)$alkyl-$(C_3-C_8)$arylene; and a is 2, wherein the alkyl moieties are optionally substituted by one or more halogen, or a pharmaceutically acceptable salt or hydrate thereof.

2. The compound of claim 1, wherein

Z is $(C_1-C_6)$alkyl.

3. The compound of claim 1, wherein:

two of X are present on adjacent atoms, and together form a six-membered aryl,

Y is halogen;

Z is $C_1-C_6$ alkyl; and

R is independently in each instance H or $C_1-C_6$ alkyl, wherein the alkyl moieties are optionally substituted by one or more halogen, or a pharmaceutically acceptable salt or hydrate thereof.

4. A compound of claim 1, wherein two of X are present on adjacent atoms, and together form a six-membered aryl optionally substituted by OH.

5. A compound of claim 1, wherein Y is a $C_1-C_6$ alkyl.

6. A compound of claim 1, wherein R is H.

7. A pharmaceutical composition comprising a compound of claim 1 and at least one pharmaceutically acceptable carrier.

8. A compound of claim 1, wherein:

Z is OH, amino, SH, N(R')$_2$, $CF_3C_1-C_6$ perfluoroalkyl, NHC(O)—$C_1-C_6$ alkyl, NHC(O)—$C_1-C_6$ perfluoroalkyl, $(C_1-C_6)$alkyl, $(C_1-C_6)$alkoxy, $(C_1-C_6)$haloalkoxy, $(C_1-C_6)$haloalkyl, $(C_2-C_6)$alkenyl, $(C_2-C_6)$alkynyl, —$NH_2$, —NH$(C_1-C_6)$alkyl, —N[$(C_1-C_6)$alkyl]$_2$, $(C_3-C_8)$heterocycloalkyl, $(C_3-C_8)$cycloalkyl, $(C_3-C_8)$aryl, $(C_3-C_8)$heterocycloalkyl-$(C_1-C_6)$alkylene-, $(C_3-C_8)$aryl$(C_1-C_6)$alkylene-, $(C_3-C_8)$aryl$(C_1-C_6)$alkenylene-, or $(C_1-C_6)$alkyl-$(C_3-C_8)$arylene.

* * * * *